(12) United States Patent
DiMauro

(10) Patent No.: US 11,304,968 B2
(45) Date of Patent: *Apr. 19, 2022

(54) PHARMACEUTICAL COMPOSITIONS COMPRISING A HYDROXYETHYLQUERCETIN GLUCURONIDE

(71) Applicant: JANSSEN PHARMACEUTICA NV, Beerse (BE)

(72) Inventor: Thomas M. DiMauro, Southboro, MA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/563,620

(22) Filed: Sep. 6, 2019

(65) Prior Publication Data

US 2020/0155584 A1    May 21, 2020

Related U.S. Application Data

(63) Continuation-in-part of application No. 16/194,283, filed on Nov. 16, 2018, now Pat. No. 10,639,294.

(51) Int. Cl.
| | |
|---|---|
| A61K 31/7048 | (2006.01) |
| A61K 47/12 | (2006.01) |
| A61K 47/18 | (2017.01) |
| A61K 9/00 | (2006.01) |
| A61K 47/46 | (2006.01) |
| A61K 47/38 | (2006.01) |
| A61K 47/42 | (2017.01) |
| A61K 47/02 | (2006.01) |

(52) U.S. Cl.
CPC ........ *A61K 31/7048* (2013.01); *A61K 9/0053* (2013.01); *A61K 47/02* (2013.01); *A61K 47/12* (2013.01); *A61K 47/186* (2013.01); *A61K 47/38* (2013.01); *A61K 47/42* (2013.01); *A61K 47/46* (2013.01)

(58) Field of Classification Search
CPC ............................ A61K 31/352; A61K 9/2009
See application file for complete search history.

(56) References Cited

U.S. PATENT DOCUMENTS

| | | | |
|---|---|---|---|
| 3,420,815 | A | 1/1969 | Courbat |
| 5,629,011 | A | 5/1997 | Illum |
| 7,166,640 | B2 | 1/2007 | Berg |
| 7,585,890 | B2 | 9/2009 | Berg |
| 8,778,894 | B2 | 7/2014 | Tan et al. |
| 10,639,294 | B2 | 5/2020 | DiMauro |
| 2003/0199446 | A1 | 10/2003 | Bunger et al. |
| 2011/0190399 | A1 | 8/2011 | Kar et al. |
| 2012/0213842 | A1 | 8/2012 | Birbara |
| 2017/0119711 | A1 | 5/2017 | Hu et al. |
| 2018/0050107 | A1 | 2/2018 | DiMauro et al. |
| 2020/0101040 | A1 | 4/2020 | DiMauro |

FOREIGN PATENT DOCUMENTS

| | | |
|---|---|---|
| AU | 3669595 | 5/1996 |
| CA | 2162299 | 11/1995 |
| CA | 2348728 A1 | 5/2000 |
| CA | 2701261 | 10/2010 |
| CN | 1663563 | 9/2005 |
| CN | 1715277 A | 1/2006 |
| CN | 1736999 A | 2/2006 |
| CN | 1884275 A | 12/2006 |
| CN | 1890232 A | 1/2007 |
| FR | 2701261 A1 | 8/1994 |
| WO | WO 2000/026399 | 5/2000 |
| WO | WO 2004/037237 A1 | 5/2004 |
| WO | WO 2008/106979 A2 | 9/2008 |
| WO | 2015169121 A1 | 11/2015 |
| WO | WO 2015/195989 A1 | 12/2015 |
| WO | WO 2017/053583 A1 | 3/2017 |

OTHER PUBLICATIONS

Notice of Allowance for U.S. Appl. No. 16/194,283, titled: "Pharmaceutical Compositions Comprising a Hydroxyethylquercetin Glucuronide Metabolite", dated Feb. 25, 2020.
"2-[3,4-dihydroxy-3,4-bis(2-hydroxyethyl)cyclohexa-1,5-dien-1-yl]-3,5,7-trihydroxy-7-(2-hydroxyethyl)-8H-chromen-4-one," www.molbase.com, CAS No. 23077-88-5, Formula: C21H26O10 (Downloaded Aug. 12, 2018).
"5-Hydroxy-213-hydroxy-4-methoxyphenyl)-4-oxo-4H-1-benzopyran-7-yl 13-D-Glucopyranosiduronic Acid Sodium; Diosmetin 7-0-Glucuronide Sodium," *Biological, Diosmetin 7-0-β-D-Glucuronide Sodium Salt CAS* (2018).
"7,3',4'-trihydroxyethylisoquercitrine-3-glucoside," CAS#:266363-39-7, Chemsrc (2018).
"Alpha-Glycosyl Isoquercitrin A Bioavailable Form of Quercetin," *Integrative Therapeutics*, integrativepro.com (2016).
"Beta-Glucuronidase in the Hydrolysis of Glucuronide-Drug Conjugates," *CovaChem Blog*, pp. 1-3 (posted 2018).
"Chemical Structure of Diosmin," Diosmin—Diosmin—Wikipedia (2018).
"Diosmetin 3'-O-β-D-glucuronide," Min. 95%—BICL4329—152503-50-9 from Apollo Scientific (2018).
"Diosmetin 7-O-β-D-Glucuronide Sodium Salt," *Diosmetin 7-O-β-D-Glucuronide Sodium Salt I SCBT—Santa Cruz Biotechnology* (2018).
"Eudramode® Datasheet," *Pharmaceutical Online, Evonik Rohm GmbH* (2018).
"β-Glucuronidase from abalone," Product Comparison Guide, 1 page, *Sigma-Aldrich* (2018).
Abdel-Salam, O. M.E., et al., "Neuroprotective and hepatoprotective effects of micronized purified flavonoid fraction (Daflon®) in lipopolysaccharide-treated rats," *Drug Discoveries & Therapeutics*, 6(6):306-314 (2012).

(Continued)

*Primary Examiner* — San Ming R Hui
(74) *Attorney, Agent, or Firm* — Hamilton, Brook, Smith & Reynolds, P.C.

(57) ABSTRACT

Disclosed herein are hydroxyethylquercetin glycosides, including compounds of Structural Formulas I, II, III and IV. The compounds disclosed are useful for inhibiting norepinephrine metabolism and treating antenatal and postnatal depression in subjects in need thereof.

19 Claims, No Drawings

(56) References Cited

OTHER PUBLICATIONS

Abou El Hassan, M.A.I., et al., "Bioavailability and Pharmacokinetics of the Cardioprotecting Flavonoid 7-monohydroxyethylrutoside in Mice," Cancer Chemother Pharmacol, 52:371-376 (2003).

Ahn-Jarvis, J. H., "Development of a Standardized Functional Soy Product for Cancer Prevention Trials: Phase II Evaluation of Isoflavone Bioavailability in Men With Asymptomatic Protate Cancer," Dissertation, The Ohio State University (2013).

Aidong, W., et al., "Pharmocokinetics of Diosmin Tablets in Healthy Human Volunteers," China Pharmacist, Jul. 2007.

Akao, T., et al., "Balicalin, the Predominant Flavone Glucuronide of Scutellariae Radix, is Absorbed from the Rat Gastrointestinal Tract as the Aglycone and Restored to its Original Form," J. Pharm. Pharmacol., 52: 1563-1568 (2000).

Al-jedai, A. H., et al., "Assessment of Fetal Risk Associated with 93 Non-US-FDA Approved Medications During Pregnancy," Saudi Pharmaceutical Journal, 20, pp. 287-299 (2012).

Almeida, A. F., "Bioavailability of Quercetin in Humans with a Focus on interindividual Variation," Comprehensive Reviews in Food Science and Food Safety, vol. 17, pp. 714-731 (2018).

Araujo, D., et al., "Diosmin Therapy Alters the in vitro Metabolism of Noradrenaline by the Varicose Human Saphenous Vein," Pharmacol. Res., 24(3):253-256 (1991).

Araujo, D., et al., "Effects of Two Venotropic Drugs on Inactivation and O-Methylation of Catecholamines in an Isolated Canine Vein," Arch. Int. Pharmacodyn. Ther., 277(2):1992-202 (1985).

Arturson, G., et al., "Stimulation and Inhibition of Biosynthesis of Prostaglandins in Human Skin by Some Hydroxyethylated Rutosides," Prostglandins, 10(6): 941-948 (1975).

Azarfarin, M., "Effects of troxerutin on anxiety- and depressive-like behaviors induced by chronic mild stress in adult male rats," Iran J Basic Med Sci, vol. 21, No. 8, (2018).

Balant, L. P., et al., "Metabolism and Pharmacokinetics of Hydroxyethylated Rutosides in Animals and Man," Reviews on Drug Metabolism and Drug Interactions, vol. 5, No. 1 (1984).

Balant, L.P., et al., "Metabolism and Pharmacokinetics of Hydroxyethylated Rutosides in Animals and Man," Q. Rev. Drug. Metab. Interact., 5(1):1-24 (1984).

Banerji, A., "Bio-inspired Syntheses of Partially Methylated Flavonoids—Untapped Source of Bioactivities," J Explor Res Pharmacol, vol. 2, Issue 1, (2017).

Banhidy, F., et al., "Congenital abnormalities in the offspring of pregnant women with type 1, type 2 and gestational diabetes mellitus: A population-based case-control study," Congenital Anomalies; 50, 115-121 (2010).

Barenys, M., et al., "Is Intake of Flavonoid-Based Food Supplements During Pregnancy Safe for the Developing Child? A Literature Review," Curr. Drug Targets, 18(2): 196-231 (2017).

Barrow, A., et al., "Metabolism of the Hydroxyethylrutosides III. The fate of Orally Administered Hydroxyethylrutosides in Laboratory Animals; Metabolism by Rat Intestinal Microflora in vitro," Xenobiotica, the fate of foreign compounds in biological systems, 4(12):473-754 (1974).

Bayandor, P., et al., "The effect of troxerutin on anxiety- and depressive-like behaviours in the offspring of high-fat diet fed dams," Archives of Physiology and Biochemistry, pp. 1-8 (2018).

Bergstein, N.A., "Clinical Study on the Efficacy of O-(β-hydroxyethyl)rutoside (HR) in varicosis of pregnancy," J. Int. Med. Res., 3(3):1898-193 (1975).

Bianchi, M., et al., "Troxerutin, a mixture of O-hydroxyethyl derivatives of the natural flavonoid rutin: Chemical stability and analytical aspects, J. Pharm. Biomed Anal., 150:248-257 (Feb. 20, 2018).

Bouktaib, M., et al., "Hemisynthesis of all the O-monomethylated analogues of quercetin including the major metabolites, through selective protection of phenolic functions," Tetrahedron, 58(50):10001-10009 (Dec. 9, 2002).

Bozoky, I., et al., "Fatigue as a Predictor of Postpartum Depression," JOGNN, 31(4), pp. 436-443 (2002).

Brad, K., et al., "Physicochemical Properties of Diosmetin and Lecithin Complex," Tropical Journal of Pharmaceutical Research, 12 (4): 453-456 (2013).

Buckshee, K., et al., "Micronized Flavonoid Therapy in Internal Hemorrhoids of Pregnancy," International Journal of Gynecology & Obstetrics, 57, pp. 145-151 (1997).

Budzianowski, J., "Six Flavonol Glucuronides From Tulipa Gesneriana," Phytochemistry, vol. 30, No. 5, pp. 1679-1682 (1991).

Budzianowski, J., et al., "Microvascular Protective Activity of Flavonoid Glucuronides Fraction from Tulipa gesneriana," Phytotherapy Research, Phytother. Res. 13, 166-168 (1999).

Butterweck, V., "Flavonoids of St. John's Wort Reduce HPA axis function in the rat.," Planta Med., 70(10):1008-11 (Oct. 2004).

Campanero, M. A., et al., "Simultaneous Determination of Diosmin and Diosmetin in Human Plasma by Ion Trap Liquid Chromatography—Atmospheric Pressure Chemical Ionization Tandem Mass Spectrometry: Application to a Clinical Pharmacokinetic Study," Journal of Pharmaceutical and Biomedical Analysis, 51, pp. 875-881 (2010).

Cao, F., et al., "Mrp2-Related Efflux of Scutellarin in the Intestinal Absorption In Rats," Pharmazie, 63, pp. 75-80 (2008).

Cao, F., et al., "The Physiochemical Characteristics of Freeze-Dried Scutellarin-Cyclodextrin Tetracomponent Complexes," Drug Development and Industrial Pharmacy, 31(8): 747-756 (2005).

Centers for Disease Control and Prevention, "Identified Prevalence of Autism Spectrum Disorder ADDM Network 2000-2014 Combining Data from All Sites," Data and Statistics, 2 pages (No Date Given).

ChemFaces Quercetin-3-O-glucuronide Datasheet, 4th Edition (Revised in Jul. 2016).

Chen, X., et al., "Pharmacokinetics and Metabolism of the Flavonoid Scutellarin in Humans After a Single Oral Administration," The American Society for Pharmacology and Experimental Therapeutics, 34(8):1345-1352 (2006).

Chen, Z., et al., "Pharmacokinetic Study of Luteolin, Apigenin, Chrysoeriol and Diosmetin After Oral Administration of Flos Chrysanthemi Extract in Rats," Fitoterapia, 83(8):1616-1622 (2012).

Chu, J-H., et al., "Pharmacokinetic Study of Scutellarin in Healthy Volunteers by Enzymatic Hydrolysis and LC-MS-MS Analysis," Chinese Pharmacological Bulletin, 31, 108-112 (2014).

Chung, Y-J., et al., "Concentration of Total and Free Choline and Betaine of Breast Milk During 5 Months of Lactation of Some Korean Lactating Women," Nutrition (American Society for Nutrition, 21(5): Apr. 2007.

Corwin, E. J., et al., "The Impact of Fatigue on the Development of Postpartum Depression," JOGNN, 34(5), pp. 577-586 (2005).

Cova, D., et al., "Pharmacokinetics and Metabolism of Oral Diosmin in Healthy Volunteers," Int. Journal of Clinical Pharm., Ther. and Tox., 30(1):29-33 (1992).

Cui, X., et al., "LC-MS-MS Determination of Troxerutin in Plasma and Its Application to a Pharmacokinetic Study," Chromatographia 73:165-169 (2011).

Davis, B., et al., Identification of Isomeric Flavonoid Glucuronides in Urine and Plasma by Metal Complexation and LC-ESI-MS/MS, J. Mass Spectrometry, (2006).

Diehl, A., "P01-27 Acetylcholinesterase-inhibitors in the treatment of tobacco dependence," European Psychiatry, 24(7), p. S415 (2009).

Diosmin, Alvolon, 500 Mg Film-Coated Tablet, Alvogen, www.alvogen.com (May 2016).

Dittrich, P., et al. "HPLC determination of troxerutin in plasma and urine following oral administration in man," Arzneimittelforschung, 35(4):765-767 (1985).

Dressman, J. B., et al., "Upper Gastrointestinal (GI) pH in Young, Healthy Men and Women," Pharmaceutical Research, vol. 7, No. 7 (1990).

Duman, M. K., et al., "Betahistine use in pregnant women with vertigo," Abstracts / Reproductive Toxicology 57, 210-227 (2015).

Duman, M.K., et al., "Diosmin-Hesperidin Use in Pregnant Women with Varicose Veins," Reproductive Toxicology, 57: 225 (Nov. 2015).

Duman, R.S., et al., "Signaling pathways underlying the rapid antidepressant actions of ketamine," Neuropharmacology, 62(1): 35-41 (Jan. 2012).

(56) References Cited

OTHER PUBLICATIONS

Eichenbaum, G., et al., "Oral Coadministration of β-glucoronidase to Increase Exposure of Extensively Glucoronidated Drugs that Undergo Enterohepatic Recirculation," J. Pharm. Sci., 101(7):2545-2556 (2012).

Erlund, I., et al., "Pharmacokinetics of Quercetin from Quercetin Aglycone and Rutin in healthy volunteers," *Eru. J. Clin. Pharmacol.*, 56:545-553 (Nov. 2000).

Ewe, K., et al., "Gastric Emptying of Indigestible Tablets in Relation to Composition and Time of Ingestion of Meals Studied by Metal Detector," Dig. Dis. Sci., 36(2): 146-152 (1991).

Ezzat, W., et al., "Role of Diosmin-Hesperidin Combination (Daflon® Servier) in Treatment of Vasomotor Rhinitis of Pregnancy; A Randomized Control Study," *Egypt. J. Otolaryngol.*, vol. 25, No. 1 (2009).

Fang, Y., et al., "Study on the Metabolism of Troxerutin by Intestinal Bacteria of the Rat in vitro," West China Journal of Pharmaceutical Sciences, Jun. 2014.

Farmae, "Flebonorm 30 Kapseln," Product Description, retrieved online at http://en.amnol.net/specialization/phlebology/flebonorm (Jul. 4, 2018).

Feng, F., "Determination of Trace Scutellarin by SPE-HPLC/MS/MS Assay and its Pharmacokinetics in Human Plasma," Journal of Chinse Pharmaceutical Sciences 41(6): 457-460 (Mar. 2006).

Flebonorm Tablets I, *Farmamica Desktop I*, https://www.farmamica.com/storeglebonorm-tablets-30g_12,html (2018).

Freag, M. S., et al., "Lyophilized phytosomal nanocarriers as platforms for enhanced diosmin delivery: optimization and ex vivo permeation," *International Journal of Nanomedicine*, 8, 2385-2397 (2013).

Frolova, N.A., et al., "Justification of the Choice of Diosmin Angioprotector as a Preventative Agent Preeclampsia," Proceedings of the Samara Scientific Center of the Russian Academy of Sciences, vol. 17, No. 2(2), 2015.

Gao, S., et al., "Highly Variable Contents of Phenolics in St John's Wort Products Impact Their Transport in the Human Intestinal Caco-2 Cell Model: Pharmaceutical and Biopharmaceutical Rationale for Product Standardization," *J Agric Food Chem.* 58(11): 6650-6659 (2010).

Gao, S.Q., et al., "Biodistribution and Pharmacokinetics of Colon-specific HPMA Copolymer—9-Aminocamptothecin Conjugate in Mice," *J Control Release*. 12; 117(2): 179-185 (2007).

Garay, R. P., et al., "Investigational drugs in recent clinical trials for treatment-resistant depression," *Expert Rev Neurother*:; 17(6): 593-609 (2017).

Garner, R.C., et al., "Comparison of the Absorption of Micronized (Daflon 500® mg) and Nonmicronized [14]C-Diosmin Tablets After Oral Administration to Healthy Volunteers by Accelerator Mass Spectrometry and Liquid Scintillation Counting," *Journal of Pharmaceutical Sciences*, vol. 91(1), pp. 32-40 (2002).

Graham, D. Y., "An Alternate Explanation of the Effect of Citric Acid on Proton Pump," AJG, 96(10):3037-3039 (2001).

Guss, J. L, et al., "Effects of Glucose and Fructose Solutions on Food Intake and Gastric Emptying in Nonobese Women," Am. J. Physiol., 267 (6 Pt 2):R1537-1544 (1994).

Hackett, A.M. et al., "Metabolism of Hydroxyethylrutosides (HR). Metabolism of [14C]-HR in man.," *Arzneimittel-Forschung*, 26(5):925-928 (Feb. 1976).

Hackett, A.M., "The Disposition and Metabolism of 3',4',7-Tri-O-(β-hydroxyethyl) rutoside and 7-Mono-O-(β-hydroxyethyl)rutoside in the Mouse," *Xenobiotica*, 7(10):641-651 (Nov. 1977).

Hackett, A.M., et al., "The Metabolism and Excretion of 7-mono-O-(β-hydroxyethyl) rutoside in the dog," *Eur. J. Drug. Metab. Pharmacokinet*, 4(4):207-212 (1979).

Hasler-Nguyen, N., et al., "Venoruton Metabolites: Pharmacological Activity and Kinetics," Phlebology 19, pp. 131-136 (2004).

Hodal, L., et al., "Detection, expression and specific elimination of endogenous β-glucuronidase activity in transgenic and non-transgenic plants," *Plant Science*, 87(7):115-122 (1992).

Hodes, G. E., "Integrating Interleukin-6 into depression diagnosis and treatment," *Neurobiology of Stress 4*, pp. 15-22 (2016).

Hornig, M., et al., "Prenatal fever and autism risk," *Molecular Psychiatry 23*, pp. 759-766 (2018).

Hostetler, G.L., et al., "Effects of Food Formulation and Thermal Processing on Flavones in Celery and Chamomile," Food Chem., 141(2): Nov. 2013.

https://elibrary.ru/item.asp?id=26021167 2/ (retrieved Oct. 6, 2018).

Hunt, J. N., et al., "The Slowing of Gastric Emptying by Nine Acids," *J. Physiol*, 201, pp. 161-179 (1969).

Hwu, J., et al., "Sodium Bis(trimethylsilyl)amide and Lithium Diisopropylamide in Deprotection of Alkyl Aryl Ethers: α-Effect of Silicon," Journal of Organic Chemistry, Jun. 1997, 62 (12) 4097-4104.

Improgo, M.R., et al., "The nicotinic acetylcholine receptor CHRNA5/A3/B4 gene cluster: dual role in nicotine addiction and lung cancer," *Prog. Neurobiol.*, 92(2):212-226 (Oct. 2010).

Iordachescu, A., et al., "Diosmetin pharmacokinetic following diosmin oral administration in man; A new study on an old product with controversial pharmacokinetic findings in the past," J Bioequiv Availab, 4.3 (2012).

Iriz, E., et al., "Effects of Calcium Dobesilate and Diosmin-Hesperidin on Apoptosis of Venous Wall in Primary Varicose Veins," Vasa, 37(3):233-240 (2008).

Jacobs, H., et al., "Differences in Pharmacological Activities of the Antioxidant Flavonoid MonoHER in Humans and Mice are Caused by Variations in its Metabolic Profile," *Clin. Pharm. & Therapeutics*, (Nov. 2011).

Jacobs, H., et al., "Identification of the Metabolites of the Antioxidant Flavonoid 7- Mono-O-(β-hydroxyethyl)-rutoside in Mice," *The American Society for Pharmacology and Experimental Therapeutics*, vol. 39, No. 5, pp. 750-756, (2011).

Jaganath, I. B., et al., "In vitro catabolism of rutin by human fecal bacteria and the antioxidant capacity of its catabolites," *Free Radical Biology & Medicine* 47, pp. 1180-1189 (2009).

Jang, S. W., et al., "A selective TrkB agonist with potent neurotrophic activities by 7,8-dihydroxyflavone," PNAS, vol. 107, No. 6, pp. 2687-2692 (2010).

Jiang, X., "Betaine, a Potent Mediator of Metabolic Programing?," *Journal of Nutritional Health & Food Engineering*, vol. 2, Issue 1 (2015).

Ju, W.Z., et al., "Determination of Scutellarin in Human Plasma by LC-MS Method and its Clinical Pharmacokinetics in Chinese Healthy Volunteers," J Clin Pharmacol Ther, Jan. 2005.

Juergenliemk, G., et al., "In Vitro Studies Indicate that Miquelianin (Quercetin 3-O-β-$_D$-Glucuronopyranoside) is Able to Reach the CNS from the Small Intestine," *Planta Med.*, 69, *Biochem., Physiol.*, pp. 1013-1017 (2003).

Jung, G., et al., "Quantitative Determination of O-(β-hydroxyethyl)-rutosides in human blood after intravenous and oral administration by circular dichroism," *European J. of Drug Metabolism and Pharmacokinetics*, 2(3):131-141 (Jul. 1977).

Juteau, N., et al., "The Human Saphenous Vein in Pharmacology: Effect of a New Micronized Flavonoidic Fraction (Daflon 500 mg) on Norepinephrine Induced Contraction," Int. Angiol., Sep. 14 (Suppl. 1 to Issue 3):8-13 (1995).

Kanaze, F. I., "Simultaneous reversed-phase high-performance liquid chromatographic method for the determination of diosmin, hesperidin and naringin in different citrus fruit juices and pharmaceutical formulations," *Journal of Pharmaceutical and Biomedical Analysis*, 33, pp. 243-249 (2003).

Kendall, S., et al., "Effects of hydroxyethylrutosides on the permeability of microvessels in the frog mesentery," *Br. J. Pharmacol.*, 110, pp. 199-206 (1993).

Khan, R. A., et al., "Behavioral effects of citrus limon in rats," *Metab Brain Dis, Research Article* (2014).

Khoury, M. J., et al., "Recurrence of Low Birth Weight in Siblings," J. Clin. Epidemiol., 42(12):1171-1178 (1989).

Kienzler, J. L., et al., "Pharmacokinetics of mono-3'- and mono-4'-0-(β-hydroxyethyl)-rutoside derivatives, after single doses of Venoruton powder in healthy volunteers," *Eur J Clin Pharmacol* 58: pp. 395-402 (2002).

(56) References Cited

OTHER PUBLICATIONS

Korniets, N.G., et al., "Clinical and Pathogenetic Substantiation of Prevention of Obstetrical Complications in Pregnant Women with Varicose Disease," Health of Woman, 6 (112), pp. 82-84; (2016).
Lacroix, I., et al., "First epidemiological data for venotonics in pregnancy from the EFEMERIS database," Phlebology, vol. 31(5) 344-348 (2016).
Lai, et al., "Comparison of Metabolic Pharmacokinetics of Baicalin and Baicalein in Rats," J. Pharm. Pharmacol., 55(2): 205-209 (2003).
Lai, M.Y., et al., "Relative Flavone Bioavailability of Scutellariae Radix between Traditional Decoction and Commercial Powder Preparation in Humans," Journal of Food and Drug Analysis, vol. 10, No. 2, pp. 75-80 (2002).
Lai, M.Y., et al., "Urinary Pharmacokinetics of Baicalein, Wogonin and Their Glycosides after Oral Administration of Scutellariae Radix in Humans," Biol. Pharm. Bull. 26(1), pp. 79-83 (2003).
Lakhno, I., "Pathogenic Peculiarities of Fetal Distress in Pregnant Women with Preeclampsia," Georgian Med News., (223):11-6 (2013).
Latif, M. H., et al., "Quantification of the components of the Iraqi Chicken wet egg yolk, and characterization of Lecithin," Chemistry and Materials Research, vol. 6 No. 6, (2014).
Lefebvre, G., et al., "Venous Insufficiency during pregnancy. Rheological improvement by Troxerutin," Rev. Fr. Gynecol Obstet, 86(2 pt. 2):206-208 (Feb. 25, 1991).
Lemmens, K.J., et al., "The contribution of the major metabolite 4'-O-methylmonoHER to the antioxidant activity of the flavonoid monoHER," Chem Biol Interact, 239:146-152 (Sep. 2015).
Lemmens, K.J., el al., "The flavonoid 7-mono-O-(β-hydroxyethyl)-rutoside is able to protect endothelial cells by a direct antioxidant effect," Toxicol in Vitro, 28(4):538-543 (Jun. 2014).
Leodolter, A., et al., "Citric Acid or Orange Juice for the $^{13}$C-Urea Breath Test: The Impact of pH and Gastric Emptying," Aliment Pharmacol Ther; 13, pp. 1057-1062 (1999).
Lesser, S. et al., "Bioavailability of Quercetin in Pigs Is Influenced by the Dietary Fat Content[1,2]," American Society for Nutritional Sciences, pp. 1508-1511 (2004).
Li, M., et al., "Safety, tolerability, and pharmacokinetics of a single ascending dose of baicalein chewable tablets in healthy subjects," Journal of Ethnopharmacology, 156, 210-215 (2014).
Liang, Y., et al., "Physical and Chemical Properties of Acetylated Low Molecular Weight Heparinand its Antineoplastic Effect in Vitro," Chinese Pharmalogical Bulletin 31(1): 108-112 (Jan. 2015).
Liu, J., et al., "Diosmetin inhibits cell proliferation and induces apoptosis by regulating autophagy via the mammalian target of rapamycin pathway in hepatocellular carcinoma HepG2 cells," Oncology Letters, 12, pp. 4385-4392 (2016).
Liu, M., et al., "Liquid chromatography/tandem mass spectrometry assay for the quantification of troxerutin in human plasma," Rapid Common. Mass Spectrom, 20: 3522-3526 (2006).
Liu, TM, et al., "Studies on the absorption kinetics of baicalin and baicalein in rats' stomachs and intestines," Zhongguo Zhong Yao Za Zhi, 31(12):999-1001 (Jun. 2006).
Lu, J., et al., "Chronic administration of troxerutin protects mouse brain against $_D$-galactose-induced impairment of cholinergic system," Neurobiol Learn Mem, 93(2):157-164 (Feb. 2010).
Maggioli, A., "Chronic venous disorders: pharmacological and clinical aspects of micronized purified flavonoid fraction," Phlebolymphology, vol. 23. No. 2., 82-91 (2016).
Malik-Wolf, B., et al., "Evaluation of Abalone β-glucoronidase Substitution in Current Urine Hydrolysis Procedures," J. Anal. Toxicol., Apr. 2014 38(3):171-176.
Marhic, C., "Clinical and Rheological Efficacy of Troxerutin in Gynecology and obstetrics," Rev Fr Gynecol Obstet, 86(2 pt. 2):209-212 (Feb. 25, 1991).
Mascarenhas, M., et al., "Revisiting the Role of First Trimester Homocysteine as an Index of Maternal and Fetal Outcome," Journal of Pregnancy, vol. 2014, Article ID 123024, pp. 1-7 (2014).

Mattarei, A., et al., "Regioselective O-Derivatization of Quercetin via Ester Intermediates. An Improved Synthesis of Rhamnetin and Development of a New Mitochondriotropic Derivative," Molecules, 15, pp. 4722-4736 (2010).
Mehndiratta, P., et al., "Formulation Development and Evaluation of Gastroresistant Microparticles of Diosmin for the Treatment of Chronic Venous Insufficiency (CVI)," International Journal of Pharma Professional's Research, vol. 6, Issue-4, (2015).
Mei, Q., et al., "Selective methylation of kaempferol via benzylation and deacetylation of kaempferol acetates," Beilstein J. Org. Chem., 11, pp. 288-293 (2015).
Menendez, C., et al., "Vascular deconjugation of quercetin glucuronide: The flavonoid paradox revealed?," Mol. Nutr. Food Res., 55, 1780-1790 (2011).
Mojaverian, P., et al., "Estimation of Gastric Residence Time of the Heidelberg Capsule in Humans: Effect of Varying Food Composition," Gastroenterology, 89, pp. 392-397 (1985).
Mono 3'-o-hydroxyethyl quercetin glucuronide q-053—Google Search (2018).
Mono-3'-o-hydroxyethylquercetin—Google Search (2018).
Murota, K., et al., "α-Oligoglucosylation of a sugar moiety enhances the bioavailability of quercetin glucosides in humans," Archives of Biochemistry and Biophysics 501, pp. 91-97 (2010).
Neerati, P., et al., "Effect of Diosmin on the Intestinal Absorption and Pharmacokinetics of Fexofenadine in Rats," Pharmacological Reports 67(2): 339-344 (2015).
Niu, XM, et al., "Acetylcholine Receptor Pathway in Lung Cancer: New Twists to an Old Story," World J. Clin Oncol, 5(4):667-676 (Oct. 10, 2014).
Non-Final Office Action for U.S. Appl. No. 16/194,283 "Pharmaceutical Compositions Comprising a Hydroxyethylquercetin Glucuronide Metabolite", dated Apr. 16, 2019.
O'Leary, K.A. et al., "Metabolism of quercetin-7- and quercetin-3-glucuronides by an in vitro hepatic model: the role of human β-glucuronidase, sulfotransferase, catechol-O-methyltransferase and multi resistant protein 2 (MRP2) in flavonoid metabolism," Biochem. Pharmacol., 65(3):479-491 (Feb. 1, 2003).
Okabe, T., et al., "Determinants of liquid gastric emptying: comparisons between milk and isocalorically adjusted clear fluids," British Journal of Anaesthesia 114 (1): 77-82 (2015).
Olthof, M. R., et al., "Low Dose Betaine Supplementation Leads to Immediate and Long Term Lowering of Plasma Homocysteine in Healthy Men and Women," American Society for Nutritional Sciences, Human Nutrition and Metabolism Research Communication, pp. 4135-4138 (2003).
Osborne, L. M., "Perinatal Depression—the Fourth Inflammatory Morbidity of Pregnancy? Theory and Literature Review," Psychoneuroendocrinology, 38(10): 1929-1952 (2013).
Osborne, L. M., et al., "Lower Allopregnanolone During Pregnancy Predicts Postpartum Depression: An Exploratory Study," Psychoneuroendocrinology 79, pp. 116-121 (2017).
Pang, H., et al., "Multiple-Ascending-Dose Pharmacokinetics and Safety Evaluation of Baicalein Chewable Tablets in Healthy Chinese Volunteers," Clin'Drug Investig, (2016).
Pang, H., et al., "Simultaneous Determination of Baicalein and Baicalin in Human Plasma by High Performance Liquid Chromatograph-Tandem Spectrometry and its Application in a Food-Effect Pharmacokinetic Study," Drug Res. (Stuttg) 66(8): 394-401 (2016).
Paput, L., et al., "Association of drug treatments in pregnant women with the risk of external ear congenital abnormalities in their offspring: A population-based case-control study," Congenital Anomalies, 51, pp. 126-137 (2011).
Park, S.W., et al., "Differential Effects of Antidepressant Drugs on mTOR Signalling in Rat Hippocampal Neurons," Int. Jour. Neuropsycopharmacology, 17, 1831-1846 (2014).
Parker-Athill, E., et al., "Flavonoids, a Prenatal Prophylaxis via Targeting JAK2/STAT3 Signaling to Oppose IL-6/MIA Associated Autism," Journal of Neuroimmunology 217, pp. 20-27 (2009).
Patten, S.B., "Propranolol and Depression: Evidence from the Antihypertensive trials," Can J. Psychiatry, 35(3):257-259 (Apr. 1990).

(56) References Cited

OTHER PUBLICATIONS

Pellock, S. J., "Glucuronides in the Gut: Sugar-Driven Symbioses Between Microbe and Host," *The American Society for Biochemistry and Molecular Biology, Inc.*, pp. 1-16 (2017).
Peng, W., et al., "Synthesis of Tamarixetin and Isorhamnetin 3-O-neohesperiodoside," Carbohydrate Research, 340(10): 1682-1688, (2005).
Penniston, K. L., "Quantitative Assessment of Citric Acid in Lemon Juice, Lime Juice, and Commercially-Available Fruit Juice Products," *J Endourol*, 22(3): 567-570 (2008).
Perrin, M., "An Update on Operative Treatments of Primary Superficial Vein Incompetence Part 2," P*hlebolymphology*, vol. 23 (2), pp. 57-120 (2016).
Posfai, E., et al., "Fetal Grown Promoting Effect of hydroxyethylrutoside in Pregnant Women," Cent. Eur. J. Med., 9(6), pp. 802-806 (2014).
Posfai, E., et al., "Teratogenic Effect of Hydroxyethylrutoside, a Flavonoid Derivative Drug—a Population-Based Case-Control Study," Journal of Maternal-Fetal & Neonatal Medicine 27(11): 1093-1098 (2014).
Repaven 1000 mg film-coated tablets (diosmin), Public Assessment Report, *Ogyei National Institute of Pharmacy and Nutrition*, pp. 13-14 (2017).
Rivas, B., et al., "Submerged Citric Acid Fermentation on Orange Peel Autohydrolysate," J. Agric. Food Chem., 9:56(7):2380-2387 (2008).
Ruijters, E.J., et al., "The cocoa flavanol (-)-epicatechin protects the cortisol response," *Pharmacol Res.*, 79:28-33 (Jan. 2014).
Russo, R., et al., "Comparative Bioavailability of Two Diosmin Formulations after Oral Administration to Healthy Volunteers," *Molecules*, 23 2174, pp. 1-9, (2018).
Russo, R., et al., "Pharmacokinetic Profile of μSMIN Plus™, a new Micronized Diosmin Formulation, after Oral Administration in Rats," vol. 10, No. 9, pp. 1569-1572 (2015).
Safety Data Sheet—Version 5.0, *Toronto Research Chemicals, Inc.* (2011).
Sakamota, A., et al., "Betaine and Homocysteine Concentrations in Infant Formulae and Breast Milk," Pediatr. Int., 43(6): 637-640 (2001).
Sasaki, Kaori, et al., "Molecular Characterization of a Novel β-Glucuronidase from Scutellaria baicalensis Georgi," The Journal of Biological Chemistry, vol. 275, No. 35, p. 27466-27472 (2000).
Schwahn, B. C., et al., "Pharmacokinetics of Oral Betaine in Healthy Subjects and Patients with Homocystinuria," *Blackwell Science Ltd Br J Clin Pharmacol*, 55, pp. 6-13 (2003).
Sclowitz, L. K. T., "Prognostic factors for low birthweight repetition in successive pregnancies: a cohort study," *Sclowitz et at BMC Pregnancy and Childbirth* 13:20 (2013).
Selectrazyme Products Technical Information Contact Company UCT [https://sampleprep.unitedchem.com/selectrazyme2/] (Retrieved Aug. 9, 2018).
Sher, E., et al., "Amine Uptake Inhibition by Diosmin and Diosmetin in Human Neuronal and Neuroendocrine Cell Lines," *Pharmacological Research*, vol. 26, No. 4, (1992).
Shu-Min, Li, "Bioequivalence of Diosmin Tablets in Healthy Volunteers," Chinese Journal of Clinical Pharmacy, Jun. 2006.
Silvestro, L., et al., "Confirmation of Diosmetin 3-O-Glucuronide as Major Metabolite of Diosmin in Humans, Using Micro-Liquid-Chromatography—Mass Spectrometry and Ion Mobility Mass Spectrometry," Anal Bioanal Chem 405, pp. 8295-8310 (2013).
Simpson, W., et al., "Relationship Between Inflammatory Biomarkers and Depressive Symptoms During Late Pregnancy and the Early Postpartum Period: A Longitudinal Study," *Revista Brasileira de Psiquiatria*, 38:190-96 (2016).
Skopp, G., et al., "Plasma Concentrations of Heroin and Morphine-Related Metabolites after Intranasal and Intramuscular Administration," *Journal of Analytical Toxicology*, vol. 21, 105-111 (1997).
Smyth, RMD, et al., "Interventions for Varicose Veins and Leg Oedema in Pregnancy (Review)," Cochrane Library Database of Systematic Reviews (2015).

Sohn, C., et al., "Effectiveness of beta-hydroxyethylrutoside in patients with Varicose Veins in Pregnancy," *Zentralbl Gynakol.*, 117(4):190-197 (1995).
Stachowicz, M., et al., "The effect of diet components on the level of cortisol," *Eur Food Res Technol*, (2016).
Stain-Texier, F., et al., "Intestinal absorption and stability of morphine 6-glucuronide in different physiological compartments of the rat," *Drug Metab. Dispos.*, 26(5):383-387 (May 1998).
Standard Deviation Formulas, How to calculate standard deviation—Google Search [https://www.google.com/search?source=hp&ei=p3LYW8SzJK2MggfA] (retrieved on Oct. 30, 2018).
Stopa, J. D., et al., "Protein disulfide isomerase inhibition blocks thrombin generation in humans by interfering with platelet factor V activation," *JCI Insight* 2(1 ):e89373. https://doi.org/10.1172/jci.insight.89373 (2017).
Taiming, L. et al., "Investigation of the Absorption Mechanisms of Baicalin and Baicalein in Rats," *Journal of Pharmaceutical Sciences*, vol. 95, No. 6, 1326-1333 (2006).
Thakral, S., et al., "Eudragit®: A Technology Evaluation," Expert Opinion Drug Deliv. 10(1)131-149(2013).
Tian, S., et al., "Pharmacokinetic Study of Baicalein After Oral Administration in Monkeys," Fitoterapia, 83(3):532-540 (2012).
Titapant, V., et al., "Trihydroxyethylrutosides in the treatment of hemorrhoids of pregnancy: a double-blind placebo-controlled trial," *J. Med. Assoc. Thai*, 84(10):1395-1400 (Oct. 2001).
TLC Pharmaceutical Standards, Product Detail, Mono-4-Hydroxyethyl-Quercetin-Glucuronide, [http://www.ticstandards.com/ProdDetail.aspx?ID=Q-054&name—QUERCETIN] retrieved Aug. 8, 2018.
Troxevasin gel 2% 100gr—pharm5.com—Pharm Trade (Jul. 12, 2018).
Udapurkar, P. P., et al., "Development and Characterization of Citrus Limon-phospholipid Complex as an Effective Phytoconstituent Delivery System," *International Journal of Life Science & Pharma Research* vol. 8, Issue 1 /(2018).
Urano, Y., et al., "Substrate-Dependent Changes of the Oxidative O-Dealkylation Mechanism of Several Chemical and Biological Oxidizing Systems," Journal of Chemical Society, Feb. 6, 1996.
Van Acker, S. A.B.E., et al., "Monohydroxyethylrutoside as protector against chronic doxorubicin-induced cardiotoxicity," *British Journal of Pharmacology* 115, 1260-1264 (1995).
Vasculera—diosmiplex 630mg https://dailymed.nim.nih.govidailymed/fda/fdaDrugXsl.cfm?setid=563d3d34-a547-47le-aecd-f4a4a57cbfld&type=display (retrieved Jul. 3, 2018).
Wellness Essentials® Pregnancy, Metagenics, Inc., [https://www.metagenics.com/wellness-essentials-pregnancy] (retrieved Jul. 3, 2018).
Werner, E., et al., "β-Glucuronidase from Helix pomatia origin is not suitable for diosmetin analysis," *Journal of Pharmaceutical and Biomedical Analysis* 53, pp. 1070-1073 (2010).
Wijayanegara, H., et al., "A clinical trial of hydroxyethylrutosides in the treatment of haemorrhoids of pregnancy," *J. Int. Med. Res.*, 20(1):54-60 (Feb. 1992).
Williams, B. J., et al., "Jak/Stat Pathway Utilized by Adrenal Cells in Response to IL-6," *Journal of Undergraduate Research* [http://jur.byu.edu/?p=9819] (2014).
Winter, J. N., et al., "ERK and Akt signaling pathways function through parallel mechanisms to promote mTORC1 signaling," *Am J Pysiol Cell Physiol 300*, C1172-C1180 (2011).
Wozniak, C.A., et al., "Native β-glucuronaidase activity in sugarbeet (*Beta vulgaris*)," *Physiologia Plantarum*, (Apr. 1994).
Wozniak, C.A., et al., "Use of β-Glucuronidase (GUS) as a Marker for Transformation in Sugarbeet," pp. 299-315, (Oct.-Dec. 1993).
Wu, B. T. F., et al., "Early Second Trimester Maternal Plasma Choline and Betaine Are Related to Measures of Early Cognitive Development in Term Infants," https://doi.org/10.1371/journal.pone.0043448, pp. 1-9 (2018).
Wu, Q. et al., "Different Antitumor Effects of Quercetin, Quercetin-3'-sulfate and quercetin-3-glucuronide in human breast cancer MCF-7 cells," *Food Funct.*, 9(3):1736-1746 (Mar. 1, 2018).
Xia, B., et al., "A Novel Local Recycling Mechanism That Enhances Enteric Bioavailability of Flavonoids and Prolongs Their Residence Time in the Gut," *Mol Pharm.* 9(11): 3246-3258 (2012).

(56) References Cited

OTHER PUBLICATIONS

Xia, C-H., et al., "Retracted: Determination of Scutellarin Isomer, a Predominant Metabolite of Scutellarin, in Human Plasma by HPLC/Tandem Mass Spectrometry and its Application to a Pharmacokinetic Study in Chinese Healthy Volunteers," Biomedical Chromatography 21(8): 5 pages (2007).

Xing, J.F., et al., "Metabolic and Pharmacokinetic Studies of Scutellarin in Rat Plasma, Urine, and Feces," *Acta Pharmacologica Sinica* 32, pp. 655-663 (2011).

Yago, M. A. R., et al., "Gastric Re-acidification with Betaine HCl in Healthy Volunteers with Rabeprazole-Induced Hypochlorhydria," *Mol Pharm*. 10(11), pp. 4032-4037 (2013).

Yamazaki, S., et al., Quercetin-3-O-glucuronide inhibits noradrenaline-promoted invasion of MDA-MB-231 human breast cancer cells by blocking β2-adrenergic signaling, *Arch Biochem Biophys*, 557:18-27 (Sep. 2014).

Yang, L., et al., "Pharmacokinetic comparison between quercetin and quercetin 3-O-β-glucuronide in rats by UHPLC-MS/MS," *Scientific Reports* 16:354-601 (2016).

Yu, F., "Study on the Metabolism of Troxerutin by Rat in vivo and in vitro," Chinese Master Thesis posted Jul. 1, 2015.

Yulan, S., et al., "Sensitive Liquid Chromatography—Tandem Mass Spectrometry Method for the Determination of Scutellarin in Human Plasma: Application to a Pharmacokinetic Study," *Journal of Chromatography B*, 830, pp. 1-5 (2006).

Zeng, X., et al., "Regioselective Glucoronidation of Diosmetin and Chrysoeriol by the Interplay of Glucuronidation and Transport in UGT1A9-Overexpressing Hela Cells," https://doi.org/10.1371/journal.pone.0166239 (2016).

Zhao, M., et al., "Determination of Metabolites of Diosmetin-7-O-Glucoside by a Newly Isolated *Escherichia coli* from Human Gut Using UPLC-Q-TOF/MS," J. Agric. Food Chem., (62): 11441-11448 Epub Nov. 17, 2014.

Zhu, Ting-ting, et al., "Pharmcokinetics of Diosmin Tablets in Healthy Volunteers," Chinese Journal of New Drugs, 2014.

Non-Final Office Action for U.S. Appl. No. 16/194,284 "Pharmaceutical Compositions Comprising a Diosmetin Glucuronide Metabolite", dated Jul. 18, 2019.

Anonymous: "Mono-3-Hydroxyethyl-Quercetin-Glucuronide", Chemical Book, Jan. 1, 2017 (Jan. 1, 2017), p. 1, XP055645324, Retrieved from the Internet: URL:https://www.chemicalbook.com/ChemicalProductProperty_ENCB02674942.htm.

Anonymous: "Mono-4-Hydroxyethyl-Quercetin-Glucuronide", Chemical Book, Jan. 1, 2017 (Jan. 1, 2017), XP055645325, Retrieved from the Internet: URL:https://www.chemicalbook.com/ChemicalProductProperty_ENCB62674944.htm.

Day, A.J., et al., "Conjugation Position of Quercetin Glucuronides and Effect on Biological Activity", Free Radical Biology & Medicine, 29(12): 1234-1243 (2000).

Notice of Allowance for U.S. Appl. No. 16/194,283, titled: "Pharmaceutical Compositions Comprising a Hydroxyethylquercetin Glucuronide Metabolite", dated Nov. 29, 2019.

Notification of Transmittal of the International Search Report and the Written Opinion of the International Searching Authority, or the Declaration for International Application No. PCT/IB2019/058343, "Pharmaceutical Compositions Comprising a Hydroxyethylquercetin Glucuronide", dated Dec. 6, 2019.

Wang, L. et al., "Characterization of soluble and insoluble-bound polyphenols from *Psidium guajava* L. leaves co-fermented with Monascus anka and *Bacillus* sp. and their bio-activities", Journal of Function Foods, 32 (2017) 149-159.

Notice of Allowance for U.S. Appl. No. 16/194,283, titled: "Pharmaceutical Compositions Comprising a Hydroxyethylquercetin Glucuronide Metabolite", dated Sep. 18, 2019.

http://tlcstandards.com/ProdDetaiLaspx?ID=Q-053&name=QUERCETIN, retrieved Nov. 1, 2019; publication date believed to be prior to Oct. 2, 2017.

http://tlcstandards.com/ProdDetaiLaspx?ID=Q-054&name=QUERCETIN, retrieved Nov. 1, 2019, publication date believed to be prior to Oct. 2, 2017.

https://www.bocsci.com/mono-4-hydroxyethyl-quercetin-glucuronide-item-483517.html, retrieved Nov. 1, 2019; original publication date unknown.

https://www.bocsci.com/mono-3-hydroxyethyl-quercetin-glucuronide-item-483515.html, retrieved Nov. 1, 2019; original publication date unknown.

Notification Concerning Transmittal of International Preliminary Report on Patentability for International Application No. PCT/IB2019/058343 "Pharmaceutical Compositions Comprising a Hydroxyethylquercetin Glucuronide" dated Apr. 15, 2021.

English Translation of WO 2015/169121 "Use of Quercetin-O-Glycoside Derivatives in Treating Lipid Metabolism Disorders", dated Apr. 11, 2019.

PHARMACEUTICAL COMPOSITIONS COMPRISING A HYDROXYETHYLQUERCETIN GLUCURONIDE

RELATED APPLICATION

This application is a continuation-in-part of U.S. application Ser. No. 16/194,283, filed Nov. 16, 2018. The entire teachings of the above application are incorporated herein by reference.

BACKGROUND

Hydroxyethylrutosides are semi-synthetic molecules that are made by reacting the phytochemical flavonoid rutin with ethylene oxide. See U.S. Pat. No. 3,420,815. Hydroxyethylrutosides have been used in Europe for the past forty years for chronic venous insufficiency and hemorrhoids under the tradenames VENORUTON® and PARAVEN™. The main components of VENORUTON® are 7-monohydroxyethylrutoside (also called MonoHER); 7,4'-dihydroxyethylrutoside; 7,3',4'-trihydroxyethylrutoside (also called troxerutin); 5,7,3',4'-tetrahydroxyethylrutoside; and 7,3',4'-trihydroxyethylquercetin. See Kendall, *Br. J. Pharmacol.*, 1993, 110, 199-206 and van Acker, *Br. J. Pharmacol.*, 1995, 115, 1260-64.

VENORUTON® is often administered several times a day in pregnant women. Titapant, *J. Med. Assoc. Thai*, 2001, October 84 (10) 1395-400 (twice daily to pregnant women for hemorrhoids); Wijayanegara, *J. Int. Med. Res.*, 1992 February, 20, 1, 54-60 (97 pregnant women; twice daily); Bergstein, *J. Intl. Med. Res.*, 1975, 3, 189-93 (69 total double blind with pregnant women; 28+ weeks, 3 times daily).

SUMMARY

Provided herein are metabolites of hydroxyethylrutosides. The compounds can be used for inhibiting norepinephrine metabolism in subjects in need thereof. Also provided herein are compositions and methods including metabolites of hydroxyethylrutosides.

One aspect is a compound comprising a metabolite of a hydroxyethylrutoside, or a pharmaceutically acceptable salt thereof. Also provided are compositions (e.g., pharmaceutical compositions), comprising a metabolite of a hydroxyethylrutoside, or a pharmaceutically acceptable salt thereof, and a pharmaceutically acceptable carrier or diluent.

In another aspect, the present disclosure provides methods of inhibiting norepinephrine metabolism in a subject in need thereof, comprising administering to the subject a compound (e.g., an effective amount of the compound) wherein the compound is a metabolite of a hydroxyethylrutoside, or a pharmaceutically acceptable salt thereof. Also provided is a compound for use in inhibiting norepinephrine metabolism, wherein the compound is a metabolite of a hydroxyethylrutoside, or a pharmaceutically acceptable salt thereof. Also provided is use of a metabolite of a hydroxyethylrutoside compound, or a pharmaceutically acceptable salt thereof, for the manufacture of a medicament for inhibiting norepinephrine metabolism.

Also provided herein is a hydroxyethylquercetin-O-glucuronide, or a pharmaceutically acceptable salt thereof. Also provided are compositions (e.g., pharmaceutical compositions) comprising a hydroxyethylquercetin-O-glucuronide, or a pharmaceutically acceptable salt thereof, and a pharmaceutically acceptable carrier or diluent.

In an aspect, the present disclosure provides methods of inhibiting norepinephrine metabolism in a subject in need thereof, comprising administering to the subject a hydroxyethylquercetin-O-glucuronide, or a pharmaceutically acceptable salt thereof (e.g., an effective amount of a hydroxyethylquercetin-O-glucuronide, or a pharmaceutically acceptable salt thereof). Also provided is a compound for use in inhibiting norepinephrine metabolism, wherein the compound is a hydroxyethylquercetin-O-glucuronide, or a pharmaceutically acceptable salt thereof. Also provided is use of a metabolite of a hydroxyethylquercetin-O-glucuronide, or a pharmaceutically acceptable salt thereof, for the manufacture of a medicament for inhibiting norepinephrine metabolism.

Another aspect is a compound comprising a hydroxyethylquercetin-7-O-glucuronide, or a pharmaceutically acceptable salt thereof. Also provided are compositions (e.g., pharmaceutical compositions) comprising a hydroxyethylquercetin-7-O-glucuronide, or a pharmaceutically acceptable salt thereof, and a pharmaceutically acceptable carrier or diluent.

In another aspect, the present disclosure provides methods of inhibiting norepinephrine metabolism in a subject in need thereof, comprising administering to the subject a compound (e.g., an effective amount of the compound) wherein the compound is a hydroxyethylquercetin-7-O-glucuronide, or a pharmaceutically acceptable salt thereof. Also provided is a compound for use in inhibiting norepinephrine metabolism, wherein the compound is a hydroxyethylquercetin-7-O-glucuronide, or a pharmaceutically acceptable salt thereof. Also provided is use of a hydroxyethylquercetin-7-O-glucuronide compound, or a pharmaceutically acceptable salt thereof, for the manufacture of a medicament for inhibiting norepinephrine metabolism.

In another aspect, the present disclosure provides methods of inhibiting norepinephrine metabolism in a subject in need thereof, comprising administering to the subject an effective amount of a composition (e.g., a pharmaceutical composition) comprising a metabolite of a hydroxyethylrutoside, or a pharmaceutically acceptable salt thereof.

In one embodiment, the composition comprises a hydroxyethylquercetin-7-O-glucuronide, or a pharmaceutically acceptable salt thereof.

In one embodiment, the composition comprises a hydroxyethylquercetin-7-O-glucuronide, or a pharmaceutically acceptable salt thereof, and a pharmaceutically acceptable carrier or diluent.

Also provided are compositions (e.g., pharmaceutical compositions) for use in inhibiting norepinephrine metabolism in a subject in need thereof, wherein the compositions comprise metabolites of hydroxyethylrutosides, or pharmaceutically acceptable salts thereof. Also provided are compositions (e.g., pharmaceutical compositions) for use in inhibiting norepinephrine metabolism in a subject in need thereof, wherein the compositions comprise a hydroxyethylquercetin-7-O-glucuronide, or a pharmaceutically acceptable salt thereof, and a pharmaceutically acceptable carrier or diluent. Also provided is use of metabolites of hydroxyethylrutosides, or pharmaceutically acceptable salts thereof, for the manufacture of a medicament for inhibiting norepinephrine metabolism in a subject. Also provided is use of a hydroxyethylquercetin-7-O-glucuronide, or a pharmaceutically acceptable salt thereof, for the manufacture of a medicament for inhibiting norepinephrine metabolism.

Another aspect is a compound of Structural Formula I:

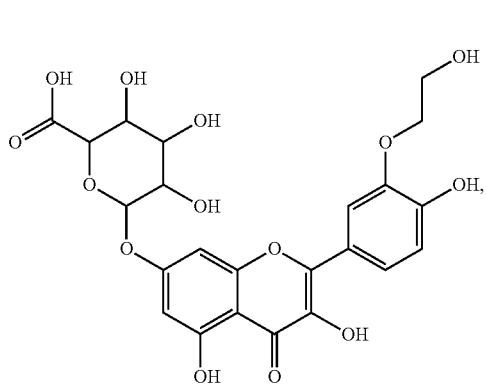

(I)

or a pharmaceutically acceptable salt thereof. Also provided are compositions (e.g., pharmaceutical compositions) comprising a compound of Structural Formula I, or a pharmaceutically acceptable salt thereof, and a pharmaceutically acceptable carrier or diluent.

In another aspect, the present disclosure provides methods of inhibiting norepinephrine metabolism in a subject in need thereof, comprising administering to the subject a compound of Structural Formula I, or a pharmaceutically acceptable salt thereof (e.g., an effective amount of the compound). Also provided is a compound for use in inhibiting norepinephrine metabolism, wherein the compound is represented by Structural Formula I, or a pharmaceutically acceptable salt thereof. Also provided is use of a compound of Structural Formula I, or a pharmaceutically acceptable salt thereof, for the manufacture of a medicament for inhibiting norepinephrine metabolism.

Another aspect is a compound of Structural Formula II:

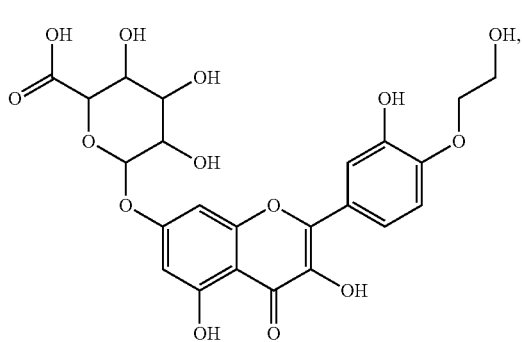

(II)

or a pharmaceutically acceptable salt thereof. Also provided are compositions (e.g., pharmaceutical compositions) comprising a compound of Structural Formula II, or a pharmaceutically acceptable salt thereof, and a pharmaceutically acceptable carrier or diluent.

In another aspect, the present disclosure provides methods of inhibiting norepinephrine metabolism in a subject in need thereof, comprising administering to the subject a compound of Structural Formula II, or a pharmaceutically acceptable salt thereof (e.g., an effective amount of the compound). Also provided is a compound for use in inhibiting norepinephrine metabolism, wherein the compound is represented by Structural Formula II, or a pharmaceutically acceptable salt thereof. Also provided is use of a compound of Structural Formula II, or a pharmaceutically acceptable salt thereof, for the manufacture of a medicament for inhibiting norepinephrine metabolism.

DETAILED DESCRIPTION

A description of example embodiments follows.

Compounds described herein include those described generally, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are incorporated herein by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its chemical structure names and rules on naming chemical structures. Optionally, a name of a compound may be generated using a chemical naming program (e.g., CHEMDRAW®, version17.0.0.206, PerkinElmer Informatics, Inc.).

Compounds of the present invention may have asymmetric centers, chiral axes, and/or chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and/or as individual diastereomers or enantiomers, with all possible isomers and mixtures thereof, including optical isomers, being included in the present invention, unless otherwise indicated.

As used herein, the indefinite articles "a," "an" and "the" should be understood to include plural referents unless the context clearly indicates otherwise. The terms "comprising," "having" and "including" are intended to be open-ended, and mean that there may be additional elements other than the listed elements.

"Ethyl" is an alkyl substituent derived from ethane ($C_2H_6$).

"Hydroxy" means —OH.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds described herein include salts derived from suitable inorganic and organic acids and bases that are compatible with the treatment of subjects.

Illustrative inorganic bases which form suitable salts include, but are not limited to, lithium, sodium, potassium, calcium, magnesium or barium hydroxides. Illustrative organic bases which form suitable salts include aliphatic, alicyclic or aromatic organic amines, such as methylamine, trimethyl amine and picoline, or ammonia. The selection criteria for the appropriate salt will be known to one skilled in the art.

Salts derived from appropriate bases include alkali metal, alkaline earth metal, ammonium and $N^+((C_1\text{-}C_4)\text{alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention. Such compounds are useful, for example, as analytical tools, as probes in biological assays, or as therapeutic agents in accordance with the present invention.

Hydroxyethylrutoside Administration in Pregnant Women

Bergstein, *J. Intl. Med. Res.*, 1975, 3, 189-93 (69 total double blind with pregnant women; 28+ weeks, 3 times daily) reported that oral administration of hydroxyethylrutosides to pregnant women with problematic varicose veins resulted in babies with good Apgar scores. Similarly, Posfai, *Cent. Eur. J. Med.*, 9, 6, 2014, 802-806 reported epidemiologically that administration of hydroxyethylrutosides to 1,143 pregnant women resulted in a significant and slight (~100 g) increase in birth weight, and a significant 40% decrease in low birth weight births. Posfai, *J. Maternal-Fetal Neonatal Medicine*, 27, 11, 2014, 1093-8 reported that, in the same data set, there was an overall 20% decrease in birth defects associated with hydroxyethylrutin use, but a slight increase in some particular ear-related birth defects associated with hydroxyethylrutin use in the first trimester. Paput, *Congenit. Anom. (Kyoto)*, 2011 September, 51, 3, 126-37 also reported ear-related birth defects amongst pregnant women using hydroxyethylrutosides, noted that over half of such cases included use during the second or third months of pregnancy, and concluded that hydroxyethylrutosides are contraindicated for pregnant women during the second and third months. Therefore, it may reasonably be concluded that it is safe to administer hydroxyethylrutosides to pregnant women in the second and third trimesters.

Other reports of hydroxyethylrutin use in pregnant women include: Titapant, *J. Med. Assoc. Thai*, 2001, October 84 (10) 1395-400 (twice daily to pregnant women for hemorrhoids; 53 patients; 16-34$^{th}$ week); Sohn, *Zentralbl. Gynakol.*, 1995, 117(4) 190-7 (17 pregnant women); Wijayanegara, *J. Int. Med. Res.*, 1992 February, 20, 1, 54-60 (97 pregnant women; twice daily); Lefebvre, *Rev Fr. Gynecol. Obstet.*, 1991 Feb. 25, 86 (2 Pt 2) 206-8 (12 pregnant women, 4 grams per day for 30 days); Marhic, *Rev. Fr. Gynecol. Obstet.*, 1991 Feb. 25, 86 (2 Pt 2) 209-12 (30 pregnant women at 4 grams/day from the 4$^{th}$ month on). None of the abstracts of these reports indicated developmental problems in the babies.

Two different hydroxyethylrutosides contained in VENORUTON® have been associated with correcting cortisol-related problems. Azarfarin, *Iran J. Basic Med. Sci.*, 2018, 21, 781-6 reported that troxerutin decreased cortisol levels in depressed, stressed rats. Ruijters, *Pharmacol. Res.*, 2014, January, 79, 28-33 reported that MonoHER (7-Mono-O-hydroxyethylrutoside) protects the proper cortisol response and decreases cortisol resistance in vitro. These reports are consistent with that of Butterweck, *Planta Med.*, 2004, October, 70(10), 1008-11, who reports that the rutin prodrugs hyperoside, isoquercetin and miquelianin each significantly downregulated circulating plasma levels of ACTH and corticosterone by 40-70% in rats.

In a related article, Bayandor, *Archives Physiol. Biochem.*, DOI:10.1080/13813455.2018.1443142, reports that administering troxerutin to pregnant rats fed a high fat diet reduced anxiety and depressive behaviors in the offspring.

Although it appears that hydroxyethylrutosides, such as troxerutin, may be beneficial to a depressed subject, the literature reports that troxerutin is associated with a high interindividual variability, whereby disparate individuals process the same troxerutin dose differently so as to end up with distinctly different levels of troxerutin metabolites in their plasma. When this occurs, some members of the group receive a healthy dose, but a significant percentage of the group receive a substantially inadequate dose.

Interindividual variation is typically represented by calculating the coefficient of variation (COV), which is defined as SD/mean, in which SD is the standard deviation associated with the mean. Typically, when the COV of a sample population is at least about 40%, the sample population is considered to have a high interindividual variation.

The literature includes references that report both the mean and standard deviation of human plasma concentrations for orally delivered hydroxyethylrutosides, such as troxerutin. They are as follows:

TABLE 1

(hydroxyethylrutoside interindividual variation)

| Author | Cmax COV | AUC COV |
|---|---|---|
| Kienzler, *Eur. J. Clin. Pharmacol.*, 2002, 58, 395-402 | 41% | 45%, 56% |
| Yu, Med. J. Nat. Def. Forces North China, 2006-04 | 49% | 48% |
| Yu, supra | 76% | 62% |
| Liu, *Rapid Comm. Mass Spectro.*, 2006, 20, 3522-26 | 35% | 56% |
| Cui, *Chromatographia* 73(1-2): 165-169 • January 2011 | 41% | 49% |
| Average | 48% | 53% |

As shown in Table 1, the COVs associated with hydroxyethylrutosides/troxerutins are about 50%, which would indicate that there is a relatively large amount of interindividual variation associated with their oral delivery in humans.

It is possible that flavone glycosides (such as troxerutin) are absorbed in each of the stomach, small intestine and colon. Whereas absorption in the stomach and small intestine is substantially direct, in the colon there are diverse levels of microbiota that first engage in reactions with the glucoside flavones (such as glucoside hydrolysis and C-ring cleavage) prior to absorption that result in the introduction of significant interindividual variation. For example, the literature reports that "there is less interindividual variation in (flavonoid glycoside) metabolites which are derived from absorption in the small intestine compared to (flavonoid glycoside) catabolites derived from the action of microbiota in the colon." Almeida, Comp Reviews Food Science Food Safety, 2018. Therefore, if there is a desire to minimize interindividual variation of orally delivered flavone glycosides, then absorption via the colon should be avoided.

Glucuronide flavones appear to absorb in the stomach and upper small intestine. For example, Xing, *Acta Pharm. Sinica*, 2011, 32, 655-663 reported that scutellarin (a flavone glucuronide) is mainly absorbed in stomach or upper small intestine. Xing further opined that the low pH of stomach favors the neutral species (as the pKa of scutellarin is about 2.7) and absorbability. Liu, Zhong Guo Zhong Yao Za Zhi, 2006 June; 31(12):999-1001 reported that baicalin (a flavone glucuronide) preferentially absorbs in the rat stomach. Taiming, J. Pharm Sci., 2006 June; 95(6):1326-33 also reported that baicalin (a flavone glucuronide) preferentially absorbs in the rat stomach. Juergenliemk, Planta Med., 2003 November, 69, 11, 1013-7 reported that miquelianin (quercetin-3-glucuronide) absorbs in the small intestine. Xia, Mol., Pharm., 2012 Nov. 5, 9, 11, 3246-58 reported that wogonoside (a flavone glucuronide) absorbs in the upper small intestine. Neither Xia nor Juergenliemk reported a stomach-based perfusion test, and so neither can exclude stomach absorption. From these reports, it is possible to determine that the small intestine/stomach wall has the enzymes necessary to cleave the glucuronic acid moiety from the flavone glucuronide to produce the absorbable aglycone, and that flavone glucuronides are preferentially absorbed from these sites.

Because glucuronide flavones appear to absorb in the stomach and upper small intestine, they may substantially avoid the colon and thereby display lower interindividual variation than their corresponding glucoside flavones (like troxerutin). A review of the literature indicates that the COVs associated with the oral delivery of flavone glucuronides are substantially less than the COVs associated with hydroxyethylrutosides (which were shown above to be about 50%; Table 1).

For example, as shown in Table 2, the average human plasma CMax COV associated with oral delivery of scutellarin (a flavone-7-O-glucuronide) is only about 33%, while the human plasma average AUC COV associated with oral delivery of scutellarin is only about 22%.

TABLE 2

(scutellarin interindividual variation)

| Author | Cmax COV | AUC COV |
|---|---|---|
| Chu, Chinese Pharmacological Bulletin, January 2015 | 36% | 22% |
| Chen Drug Metab Dispos. 2006 August; 34(8): 1345-52 | 33 | 33% |
| Feng/Yulan, J. Chromotog. B, 830, 2006, 1-5 | 19 | 12 |
| Feng/Yulan, supra | 23 | 16 |
| Ju, "Det'n of scutellarin . . . ", January 2005 | 55 | 28 |
| Average | 33% | 22% |

Similarly, the COVs for human urinary concentrations associated with the oral delivery of flavone glucuronides are also low. Lai, Biol. Pharm. Bull., 26,1,2003, 79-93, reported that oral delivery of baicalin/wogonoside (each being a flavone-7-O-glucuronide) in humans produce very low urinary COVs. Lai reported the oral intake of a dose of baicalin 616 mg and baicalein 52.5 mg (so that 90% of the baicalin/baicalein dose was baicalin), and found that the baicalin metabolites gave a urinary COV of about 10%. Lai also reported the oral intake of a dose of wogonoside (117.2 mg) and wogonin (32 mg) (so that 80% of the wogonoside dose was wogonoside) and again found that the wogonoside metabolites gave a urinary COV of about 10%.

Because the literature reports that oral delivery in humans of flavone-7-O-glucuronide phytochemicals produce very low plasma and urinary COVs, it would appear that oral delivery of the 7-O-glucuronide metabolites of hydroxyethylrutosides would likely also yield low COVs.

Therefore, the present invention solves the issue of high interindividual variation problems associated with the hydroxyethylrutosides by providing metabolites of the parent molecules in glucuronide form.

Despite the presence of the glucuronide group, it is known that flavone-7-glucuronides are not very water soluble. For example, Chen, Cancer Lett. 2014 Nov. 1; 354(1): 5-11, reported that baicalin is poorly soluble in water, while Xiao, Eur J Pharm Sci. 2016 Oct. 10; 93:456-67 reported that scutellarin is poorly soluble in water. Therefore, it may reasonably be determined that hydroxyethylquercetin-7-O-glucuronides are likewise poorly soluble in water. This lack of water solubility may impact the ability of the 7-O-glucuronide to approach neighboring cells containing the glucuronidase necessary for the deconjugation required to pass through the stomach/small intestine wall. Therefore, in some embodiments, the hydroxyethylquercetin glucuronide is in the form of a salt, such as a sodium salt. In some embodiments, the salt can be made by simply mixing stoichiometric amounts of the glucuronide and sodium hydroxide or sodium bicarbonate. It is believed that the salt of the glucuronide will be suitably water soluble, thereby improving the oral bioavailability of the glucuronide.

This lack of water solubility may impact the ability of the glucuronide to approach neighboring cells containing the glucuronidase necessary for the deconjugation required to pass through the GI tract wall. Therefore, in some embodiments, the mono -3'-O-hydroxyethylquercetin-glucuronide is in the form of a salt, such as a sodium salt. Therefore, in some aspects, there is provided a pharmaceutical composition comprising a salt comprising hydroxyethylquercetin-7-O-glucuronate and a pharmaceutically acceptable carrier. In some embodiments, the hydroxyethylquercetin-7-O-glucuronate is a monohydroxyethylquercetin -7-O-glucuronate.

As explained above, at least two investigators (Liu and Taiming) report that flavone glucuronides are preferentially absorbed in the stomach. Because the stomach lacks the microbiota associated with high interindividual variation, it is believed that the preferential absorption in the substantially microbe-free stomach may be the reason for the low interindividual variation of flavone glucuronides. Therefore, in some embodiments, the present disclosure provides compositions designed to increase stomach absorption of the flavone glucuronide.

One way to increase stomach absorption of the flavone glucuronide is to increase the residence time of the molecule in the stomach. The literature reports that having a meal increases the emptying time of the stomach contents. However, those meals typically raise the pH of the stomach contents to about 3-4 (i.e., above the pKa of the flavone glucuronide) and so also have the effect of substantially reducing the amount of the absorption-favorable protonated species of the flavone glucuronide. Thus, the following problem is encountered:
  a fasting stomach has a low pH, yielding the desired protonated (neutral) glucuronide form but will empty water in only 15 minutes (t½) (Okabe, Brit. J. Anasthesia, 114, 1, 77-82, 2015), thereby allowing only 15 minutes of glucuronide exposure in the stomach;
  a fed stomach has a long gastric emptying time (~3 hours) but its higher pH yields the undesired anionic glucuronide form that poorly absorbs.

Therefore, there is presented a challenge of delivering the desired neutral glucuronide with a long residence time in the stomach.

In an effort to solve this problem, it was observed that 200 ml of a pH 2 Acid solution (e.g., 0.1 N citric acid) will increase gastric emptying time (t½) to 60 minutes. Leodolter, *Aliment Pharmacol. Ther.*, 1999 August, 13(8), 1057-62. This amounts to a four-fold increase in gastric emptying time. Thus, in some embodiments, there is provided a method in which about 300 ml of low pH acidic media (e.g., 0.1 N citric acid (~6 g per liter); white vinegar (pH 2.4) or lime juice (pH 2-2.5)) is used as the oral liquid media when orally taking the glucuronide compositions of the present invention. If the combination of the composition and the low pH acidic media are taken on an empty stomach, this will have the effect of increasing gastric residence time of the glucuronide while retaining the glucuronide (which likely has a pKa of about 2.7) in its protonated form.

In other embodiments, about 450 mg of betaine HCl (pH ~1) can be used as the acidifier.

It is believed that providing an increased volume of low pH gastric contents will likewise help the salt pharmacokinetics, as the low pH will help ensure the glucuronate anion formed by dissolution of the salt will be converted into the neutral glucuronide species that is better able to absorb through the stomach wall than the anionic glucuronate form formed upon salt dissolution.

Compounds

One aspect is a compound comprising a metabolite of a hydroxyethylrutoside (e.g., a monohydroxyethylrutoside, a dihydroxyethylrutoside, a trihydroxyethylrutoside), or a pharmaceutically acceptable salt thereof. In one embodiment, the compound is a metabolite of troxerutin.

Another aspect is a compound comprising a hydroxyethylquercetin glycoside (e.g., a monohydroxyethylquercetin glycoside, a dihydroxyethylquercetin glycoside, a trihydroxyethylquercetin glycoside), or a pharmaceutically acceptable salt thereof. In a specific aspect, the hydroxyethylquercetin glycoside is a monohydroxyethylquercetin glycoside (e.g., a mono-3'-O-hydroxyethylquercetin glycoside, a mono-4'-O-hydroxyethylquercetin glycoside, a mono-7-O-hydroxyethylquercetin glycoside, a monohydroxyethylquercetin glucuronide). Mono-4'-hydroxyethylquercetin glucuronide is available from BOC Sciences, Shirley, N.Y., 11967, as item 483517.

As used herein, "glycoside" refers to a compound comprising a sugar moiety that is attached to the compound via a glycosidic bond. Thus, when glycoside follows a compound name (e.g., hydroxyethylquercetin), "glycoside" modifies the particular compound described by the name, such that the modified compound includes a sugar moiety that is attached to the compound via a glycosidic bond. A sugar moiety of a glycoside can be a monosaccharide or a polysaccharide. Examples of glycosides include, but are not limited to, glucuronide, glucoside and rutinose. In some embodiments, the glycoside is a glucuronide. In some embodiments, the glycoside is a glucoside.

In some aspects, the hydroxyethylquercetin glycoside is a hydroxyethylquercetin -3-O-glycoside (e.g., a hydroxyethylquercetin-3-O-glucuronide, such as mono -3'-O-hydroxyethylquercetin-3-O-glucuronide or mono-4'-O-hydroxyethylquercetin-3-O-glucuronide).

In some aspects, the hydroxyethylquercetin glycoside is a hydroxyethylquercetin-5-O-glycoside (e.g., a hydroxyethylquercetin-5-O-glucuronide, such as mono-3'-O-hydroxyethylquercetin -5-O-glucuronide or mono-4'-O-hydroxyethylquercetin-5-O-glucuronide).

In some aspects, the hydroxyethylquercetin glycoside is a hydroxyethylquercetin-7-O-glycoside (e.g., a hydroxyethylquercetin-7-O-glucuronide, such as mono-3'-O-hydroxyethylquercetin -7-O-glucuronide or mono-4'-O-hydroxyethylquercetin-7-O-glucuronide).

In some aspects, the hydroxyethylquercetin glycoside is a hydroxyethylquercetin-3'-O-glycoside (e.g., a hydroxyethylquercetin-3'-O-glucuronide, such as mono-7-O-hydroxyethylquercetin -3'-O-glucuronide).

In some aspects, the hydroxyethylquercetin glycoside is a hydroxyethylquercetin-4'-O-glycoside (e.g., a hydroxyethylquercetin-4'-O-glucuronide, such as mono-7-O-hydroxyethylquercetin -4'-O-glucuronide).

In some aspects, the glycoside component of mono-3'-O-hydroxyethylquercetin-glycoside is a glucuronide. In some embodiments, the glucuronide component is a 7-O-glucuronide (thereby producing mono-3'-O-hydroxyethylquercetin-7-O-glucuronide; see Structural Formula I). In other aspects, the glycoside component of mono -3'-O-hydroxyethylquercetin-glycoside is a glucoside. Mono-3'-hydroxyethylquercetin -7-O-glucuronide is available from Sinco Pharmachem Inc., West Bloomfield Township, Mich.

One aspect is a compound comprising a hydroxyethylquercetin-7-O-glucuronide, or a pharmaceutically acceptable salt thereof.

Another aspect is a compound represented by Structural Formula I:

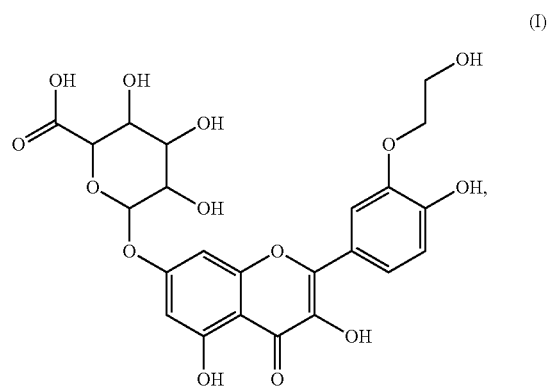 [SMILES: O=C(O)C1OC(Oc2cc(O)c3c(=O)c(O)c(-c4ccc(O)c(OCCO)c4)oc3c2)C(O)C(O)C1O]

or a pharmaceutically acceptable salt thereof.

A second aspect is a compound represented by Structural Formula II:

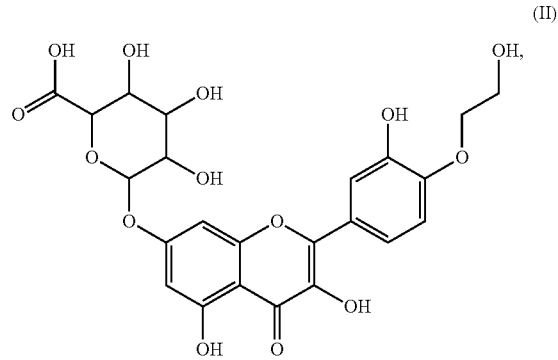 [SMILES: O=C(O)C1OC(Oc2cc(O)c3c(=O)c(O)c(-c4ccc(OCCO)c(O)c4)oc3c2)C(O)C(O)C1O]

or a pharmaceutically acceptable salt thereof.

A third aspect is a compound represented by Structural Formula III:

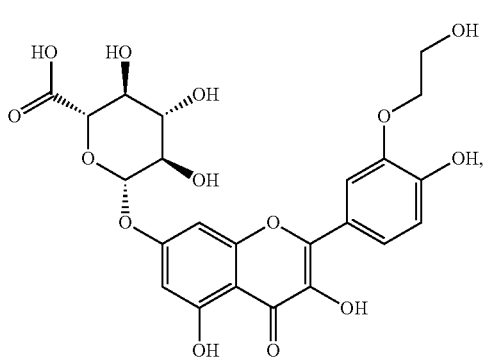

or a pharmaceutically acceptable salt thereof.

A fourth aspect is a compound represented by Structural Formula IV:

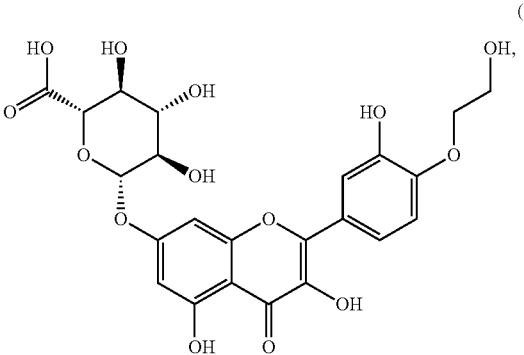

or a pharmaceutically acceptable salt thereof.

Troxerutin is a compound represented by Structural Formula V:

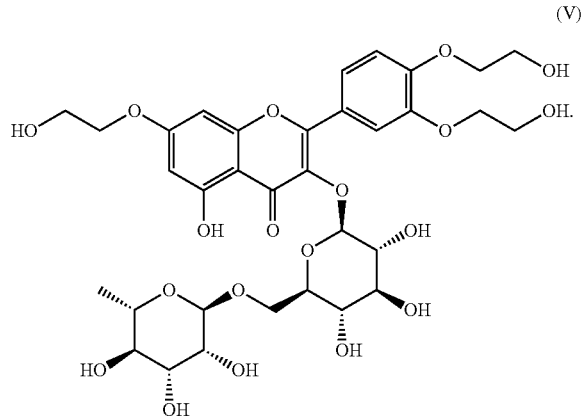 [SMILES: C[C@@H]1O[C@@H](OC[C@H]2O[C@@H](Oc3c(-c4ccc(OCCO)c(OCCO)c4)oc4cc(OCCO)cc(O)c4c3=O)[C@H](O)[C@@H](O)[C@@H]2O)[C@H](O)[C@H](O)[C@H]1O]

Compositions

Provided herein are compositions (e.g., pharmaceutically acceptable compositions) comprising one or more compounds disclosed herein (e.g., a metabolite of a hydroxyethylrutoside, a hydroxyethylquercetin-7-O-glucuronide, a compound of any of Structural Formulas I-IV), or a pharmaceutically acceptable salt thereof, and a pharmaceutically acceptable carrier or excipient. In certain embodiments, a composition of the invention is formulated for administration to a subject (e.g., a patient) in need of the composition. In some embodiments, a composition of the invention is formulated for oral, intravenous, subcutaneous, intraperitoneal or dermatological administration to a subject in need thereof.

In some embodiments, a composition of the invention further comprises a second acid. In one embodiment, the second acid is selected from citric acid, hydrochloric acid, and a combination thereof. As one skilled in the art would understand, the glucuronide compounds described herein are acids (i.e., a first acid) in the described compositions, therefore, a second acid can be added to the composition. Without wishing to be bound by any particular theory, it is believed that that the second acid increases gastric residence time of the compound in its protonated (neutral) form when administered.

The phrase "pharmaceutically acceptable carrier or excipient" refers to a non-toxic carrier or excipient that does not destroy the pharmacological activity of the agent with which it is formulated and is nontoxic when administered in doses sufficient to deliver a therapeutic amount of the agent. Pharmaceutically acceptable carriers or excipients that may be used in the compositions described herein include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives, such as hydroxyalkylcyclodextrins, including 2- and 3-hydroxypropyl-β-cyclodextrins, or other solubilized derivatives, can also be advantageously used to enhance delivery of agents described herein.

Compositions described herein may be administered by parenterally or non-parenteral means of administration, including, for example, orally, parenterally, by inhalation (e.g., intrabronchial, intranasal or oral inhalation, intranasal drops), topically, rectally, nasally, buccally, vaginally, dietarily, transdermally or via an implanted reservoir. In some embodiments, provided compounds or compositions are administrable intravenously and/or intraperitoneally. Administration can be local or systemic as indicated. The preferred mode of administration can vary depending on the particular compound chosen.

The term "parenteral" or "parenterally", used interchangeably herein, includes injection, subcutaneous, intracutaneous, intravenous, intramuscular, intradermal, intraocular, intravitreal, intra-articular, intra-arterial, intrasynovial, intrasternal, intrathecal, intralesional, intrahepatic, intraperitoneal intralesional and intracranial injection or infusion techniques.

Compositions provided herein can be orally administered in any orally acceptable dosage form including, but not limited to, capsules, tablets, pills, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound described herein can also be in microencapsulated form with one or more excipients. In such solid dosage forms, the compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, a compound described herein can be provided in an extended (or "delayed" or "sustained") release composition. This delayed-release composition comprises the compound in combination with a delayed-release component. Such a composition allows targeted release of a provided agent into the lower gastrointestinal tract, for example, into the small intestine, the large intestine, the colon and/or the rectum. In certain embodiments, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH-dependent polymers, by hydrogel plugs swelling with time (Pulsincap), by time-dependent hydrogel coatings and/or by acrylic acid linked to azoaromatic bonds coatings.

Compositions described herein can also be administered in the form of suppositories for rectal administration. These can be prepared by mixing a compound described herein with a suitable non-irritating excipient that is solid at room temperature but liquid at rectal temperature and, therefore, will melt in the rectum to release the drug. Such materials include cocoa butter, beeswax and polyethylene glycols.

For ophthalmic use, compositions can be formulated as micronized suspensions in isotonic, pH adjusted sterile saline, or, for example, as solutions in isotonic, pH adjusted sterile saline, either with or without a preservative such as benzylalkonium chloride. Alternatively, for ophthalmic use, the compositions can be formulated in an ointment such as petrolatum.

Compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

The amount of a compound described herein that can be combined with the carrier materials to produce a composition in a single dosage form will vary depending upon the subject treated, the particular mode of administration and the activity of the agent employed. Compositions can be formulated so that a dosage of from about 0.01 mg/kg to about 100 mg/kg body weight/day of the agent can be administered to a subject receiving the composition.

It should also be understood that a specific dosage and treatment regimen for any particular patient will depend upon a variety of factors, including the activity of the specific agent employed, the age, body weight, general health, sex, diet, time of administration, rate of excretion, drug combination, the judgment of the treating physician and the severity of the particular disease/disorder being treated. The amount of a compound in the composition will also depend upon the particular compound in the composition.

The compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

In some embodiments, compositions comprising a compound described herein (e.g., a metabolite of a hydroxyethylrutoside, a hydroxyethylquercetin-7-O-glucuronide, a compound of any of Structural Formulas I-IV), or a pharmaceutically acceptable salt thereof, can also include one or more other therapeutic agents. When the compositions of this invention comprise a combination of a compound described herein and one or more other therapeutic agents, the agents should be present at dosage levels of between about 1 to 100%, and more preferably between about 5% to about 95% of the dosage normally administered in a monotherapy regimen. The additional agent(s) can be part of a single dosage form, mixed together with the compound described herein, or a pharmaceutically acceptable salt thereof, in a single composition. Alternatively, the additional agent(s) can be administered separately, as part of a multiple dose regimen, from the compound described herein, or a pharmaceutically acceptable salt thereof.

Thus, also provided is a kit comprising a compound described herein (e.g., a metabolite of a hydroxyethylrutoside, a hydroxyethylquercetin-7-O-glucuronide, a compound of any of Structural Formulas I-IV), or a pharmaceutically acceptable salt thereof, and an additional agent(s) (e.g., a second acid). In one embodiment, the kit comprises an effective amount of a compound described herein, or a pharmaceutically acceptable salt thereof, to treat a disease, disorder or condition described herein, and an effective amount of an additional agent(s) to treat a disease, disorder or condition described herein.

The compositions described herein can, for example, be administered by any of the methods described herein, including injection, intravenously, intraarterially, intraocularly, intravitreally, subdermally, orally, buccally, nasally, transmucosally, topically, in an ophthalmic preparation, or by inhalation, with a dosage ranging from about 0.5 mg/kg to about 100 mg/kg of body weight or, alternatively, in a dosage ranging from about 1 mg/dose to about 5000 mg/dose or from about 1 mg/dose to about 1,000 mg/dose, every 4 to 120 hours (e.g., about every 24 hours), or according to the requirements of the particular drug. In one embodiment, the dosage is about 450 mg/dose. Typically, the compositions will be administered from about 1 to about 6 (e.g., 1, 2, 3, 4, 5 or 6) times per day or, alternatively, as a continuous infusion. The amount of active ingredient that can be combined with a carrier material to produce a single dosage form will vary depending upon the subject treated and the particular mode of administration. A typical preparation will contain from about 5% to about 95% active compound (w/w). Alternatively, a preparation can contain from about 20% to about 80% active compound (w/w).

Doses lower or higher than those recited above may be required. Specific dosage and treatment regimens for any particular patient will depend upon a variety of factors, including the activity of the specific agent employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a subject's condition, a maintenance dose of a compound (e.g., a metabolite of a hydroxyethylrutoside, a hydroxyethylquercetin-7-O-glucuronide, a compound of any of Structural Formulas I-IV), or a pharmaceutically acceptable salt thereof, composition or combination of this invention can be administered, if necessary. Subsequently, the dosage or frequency of administration, or both, can be reduced, as a function of the symptoms, to a level at which the improved condition is retained when the symptoms have been alleviated to the desired level. Subjects may, however, require intermittent treatment on a long-term basis upon recurrence of disorder symptoms.

Methods

Kienzler, *Eur. J. Clin. Pharmacol.*, 2002, 58, 395-402 reported that oral administration of hydroxyethylrutoside-containing VENORUTON® in human volunteers results in detectable plasma levels of two major metabolites—mono-3'-O-hydroxyethyl quercetin-glucuronide (Mono-3'-O-HEQG) and mono-4'-O-hydroxyethylquercetin-glucuronide.

Mono-3'-O-HEQG is attractive as a monotherapy because i) as a hydroxyethylquercetin-containing compound, it likely has the same beneficial effects as troxerutin and MonoHER upon cortisol, and so may be useful in treating antenatal or postpartum depression, and ii) it has an exceptionally long terminal half-life of at least 17 hours (Kienzler, *Eur. J. Clin. Pharmacol.*, 2002, 58, 395-402 FIG. 2), thereby possibly allowing for only a single administration a day. A single administration per day would represent an improvement in ease of use over the current multiple administrations per day of hydroxyethylrutosides.

However, there are some pharmacology issues with Mono-3'-O-HEQG. Although Kienzler reports the detection of Mono-3'-O-HEQG as a VENORUTON® metabolite, when the VENORUTON® was provided in low (0.5 g) doses, the Mono-3'-O-HEQG was detectable in only 13 of the 16 volunteers. Similarly, Hasler-Nguyen, *Phlebology*, 2004, 19, 131-6, attempted oral administration of deglycosylated VENORUTON® (i.e., hydroxyethylquercetins) to rats, and reported that Mono-3'-O-HEQG was not detectable. Therefore, it appears that oral administration of conventional mixtures of HEQ-containing compositions cannot reliably produce the described Mono-3'-O-HEQG molecule as a metabolite in the plasma.

It further appears that the way to reliably produce Mono-3'-O-HEQG in the blood stream is to avoid having to rely on the liver to produce it from starting materials that do not include molecules solely hydroxylethylated at the 3' position. Rather, the way to reliably produce the molecule is to administer a rutin-based molecule solely hydroxylethylated at the 3' position.

Provided herein are methods for attaining detectable levels of mono-3'-O-hydroxyethylquercetin glucuronide in a subject, comprising administering a mono-3'-O-hydroxyethylquercetin-glycoside or a pharmaceutically acceptable salt thereof and a pharmaceutically acceptable carrier or diluent to the subject. Also provided are methods of reliably attaining detectable levels of Mono-3'-O-HEQG, comprising orally administering a composition comprising mono-3'-O-hydroxyethylquercetin and a pharmaceutically acceptable carrier.

Without wishing to be tied to a theory, it is expected that the mono-3'-O-hydroxyethylquercetin-glycoside (estimated log P=0-1) will be more water soluble than mono -3'-O-hydroxyethylquercetin (estimated log P=2-3) while still being able to traverse cell walls, and so will likely be more bioavailable.

It is expected that mono-3'-O-hydroxyethylquercetin-glycoside may be cleaved in the colon by colonic microbiota to produce mono-3'-O-hydroxyethylquercetin (Mono-3'-O-HEQ). From there, it is expected that Mono-3'-O-HEQ will travel through the colon wall to the liver where it will be glucuronidated to become mono-3'-O-hydroxyethylquercetin glucuronide again. Jaganath., *Free Rad. Biol. Med.*, 47, 2009, 1180-9, reports that rutin is cleaved by bacteria microflora in the colon, and Barrow, *Xenobiotica*, May 1974, 743-54, reports that hydroxyethylrutosides are cleaved in the colon by microflora. However, there is at least some evidence that glucuronides can be absorbed in the small intestine. Stain-Texier, *Drug Metab Dispos.*, 1998 May, 26, 5, 383-7. One recent paper (Yang, *Scientific Reports*, 6:35460, 2016) examined the similar molecule quercetin-3-glucuronide and indicated that it is processed either by deconjugation by luminal lactase phlorizin hydrolase or by intestinal microflora before absorption into the blood. Thus, it is relatively clear that mono-3'-O-hydroxyethylquercetin-glycoside will be cleaved in the GI tract, but it is somewhat uncertain where that cleavage will occur. It may be that glycosides containing two sugars are cleaved in the colon while glycosides containing one sugar are cleaved in the small intestine.

Hydroxyethylrutosides may be useful in preventing postpartum depression by enhancing norepinephrine levels in the brain. Hydroxyethylrutosides prevent metabolism of norepinephrine, thereby prolonging norepinephrine life (and increasing venous tone). See Araujo, Arch. *Int., Pharmacoldyn., Ther.*, 1985 October, 277, 2, 192-202 (VENORUTON® blocks norepinephrine inactivation). Norepinephrine is associated with alertness. Strahler, *Biol Psychol.* 2013 September; 94(1):160-6. doi: 10.1016/j.biopsycho.2013.06.002. Epub 2013 Jun. 13, examined the norepinephrine and epinephrine responses to physiological and pharmacological stimulation in chronic fatigue syndrome (CFS) and concluded that inadequate catecholaminergic responses to physical exertion might contribute to CFS symptoms. Blier, *Neuropsychiatr Dis Treat.* 2011; 7(Suppl 1): 15-20 reported that dampening of the activity of norepinephrine and dopamine neurons through inhibitory 5-HT2A and 5-HT2C receptors, respectively, could explain residual symptoms of fatigue, lack of energy, and anhedonia in depressed patients taking SSRIs. There are also studies that conclude that postpartum fatigue predicts postpartum depression. In a study of 37 postpartum women, 13 of the 14 who rated themselves as significantly fatigued at 2 weeks postpartum went on to develop symptoms of PPD at 1 month postpartum. Bozosky, J. Obstet. Gynec., *Neonatal Nursing*, 31, 2002, 436-443. Significant correlations were obtained between postpartum fatigue and symptoms of PPD on days 7, 14 and 28, with day 14 fatigue levels predicting future development of PPD in 10 of 11 women. Corwin, *J. Obstet. Gynec.*, Neonatal Nursing, 2005, September-October, 34, 5, 557-86. Fatigue and depressive symptoms were moderately to strongly correlated at 1, 3 and 6 months postpartum. Doering-Runquist, "Severe Fatigue and Depressive Symptoms in lower-Income Urban Postpartum Women", *Western J Nurs Res.*, 2009.

Provided herein are methods of inhibiting norepinephrine metabolism in a subject in need thereof, comprising administering to the subject an effective amount of a compound described herein (e.g., a metabolite of a hydroxyethylrutoside, a hydroxyethylquercetin -7-O-glucuronide, a compound of any of Structural Formulas I-IV), or a pharmaceutically acceptable salt thereof, or a composition comprising an effective amount of a compound described herein, or a pharmaceutically acceptable salt thereof.

Also provided herein are methods of treating depression in a subject in need thereof, comprising administering to the subject an effective amount of a compound described herein (e.g., a metabolite of a hydroxyethylrutoside, a hydroxyethylquercetin-7-O-glucuronide, a compound of any of Structural Formulas I-IV), or a pharmaceutically acceptable salt thereof, or a composition comprising an effective amount of a compound described herein, or a pharmaceutically acceptable salt thereof.

Administration of hydroxyethylrutosides appear to be safe for pregnant women and correct cortisol-related problems; as such, also provided herein are methods of treating perinatal, antenatal (i.e., prenatal) and/or postpartum depression in a subject in need thereof, comprising administering to the subject an effective amount of a compound described herein (e.g., a metabolite of a hydroxyethylrutoside, a hydroxyethylquercetin-7-O-glucuronide, a compound of any of Structural Formulas I-IV), or a pharmaceutically acceptable salt thereof, or a composition comprising an effective amount of a compound described herein, or a pharmaceutically acceptable salt thereof.

The terms "treat" and "treatment" refer to therapeutic treatment, wherein the object is to slow down (lessen) an undesired physiological change or disease, or provide a beneficial or desired clinical outcome during treatment. Beneficial or desired clinical outcomes include alleviation of symptoms, diminishment of extent of disease/disorder, stabilization (i.e., not worsening) of disease/disorder, delay or slowing of disease/disorder progression, amelioration or palliation of the disease/disorder state, and/or remission (whether partial or total), whether detectable or undetectable. Those in need of treatment include those subjects already with the undesired physiological change or disease/disorder as well as those subjects prone to have the physiological change or disease/disorder.

In an embodiment, the subject (e.g., patient) is a mammal (e.g., human, non-human primate, cow, sheep, goat, horse, dog, cat, rabbit, guinea pig, rat, mouse or other bovine, ovine, equine, canine, feline, or rodent organism). In one embodiment, the subject is a human. In one embodiment, the subject is a pregnant human. In some embodiments, the pregnant human is in the second or third trimester. In some embodiments, the pregnant human is in the third trimester. In some embodiments, the pregnant human is in the second trimester. In some embodiments, the subject's pregnancy is at about the 20th to 28th week of gestation. In some embodiments, the subject is a human that has given birth about 1 to about 4 weeks prior. In one embodiment, the subject is a postnatal human. In some embodiments, the human is postpartum. In some embodiments, the human has given birth no more than about 4 weeks earlier, or the human has given birth no more than about 1 week earlier.

A "subject in need thereof" refers to a subject who has, or is at risk for developing, a disease or condition described herein (e.g., depression and/or norepinephrine metabolism imbalance). A skilled medical professional (e.g., physician or clinician) can determine whether a subject has, or is at risk for developing, a disease or condition described herein (e.g., depression and/or norepinephrine metabolism imbalance).

A "therapeutically effective amount" or "effective amount", used interchangeably herein, refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Example indicators of an effective therapeutic or combination of therapeutics that include, for example, improved well-being of the patient or reduction of symptoms of depression.

An effective amount of the compound to be administered can be determined by a clinician of ordinary skill using the guidance provided herein and other methods known in the art, and is dependent on several factors including, for example, the particular compound and/or compositions chosen, the subject's age, sensitivity, tolerance to drugs and overall well-being. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and disease is well within the abilities of one of skill in the art. Preferably, the dosage does not cause or produces minimal adverse side effects (e.g., immunogenic response, nausea, dizziness, gastric upset, hyperviscosity syndromes, congestive heart failure, stroke, pulmonary edema).

A compound described herein (e.g., a metabolite of a hydroxyethylrutoside, a hydroxyethylquercetin-7-O-glucuronide, a compound of any of Structural Formulas I-IV), or a pharmaceutically acceptable salt thereof, can be administered in a single dose or as multiple doses, for example, in an order and on a schedule suitable to achieve a desired therapeutic effect (e.g., inhibiting norepinephrine metabolism). Suitable dosages and regimens of administration can be determined by a clinician of ordinary skill.

In some embodiments, the administration of the compounds/compositions of the invention can include administration of an acidifier, such as, e.g., betaine, or a pharmaceutically acceptable salt thereof, or an acidic liquid media. In one embodiment, the acidic liquid media has a pH of less than about 3. In one embodiment, the acidic liquid media comprises citric acid, acetic acid, or hydrochloric acid, or a combination of any of the foregoing. In one embodiment, the acidic liquid media comprises vinegar or a citrus juice, or a combination of the foregoing. Examples of other acids useful herein include hydrobromic acid, phosphoric acid, sulfuric acid, perchloric acid, oxalic acid, maleic acid, tartaric acid, succinic acid and malonic acid.

The acidifier or acidic liquid media is provided to increase the gastric residence time of the compound in its protonated form. A fasting stomach has a low pH, yielding the desired protonated (neutral) glucuronide form, but will empty water in 15 minutes (Okabe, Brit. J. *Anasthesia*, 114, 1, 77-82, 2015), thereby allowing only 15 minutes of compound (i.e., glucuronide) exposure in the stomach. Conversely, a fed stomach has a long gastric emptying time (3 hours), but its higher pH yields an undesired anionic glucuronide form that poorly absorbs. Thus, it is desirable to deliver the desired neutral glucuronide with a long residence time in the stomach. As such, an acidifier and/or acidic liquid media is provided with the composition to increase the gastric residence time of the glucuronide in its protonated (neutral) form and to increase its solubility.

A compound described herein (e.g., a metabolite of a hydroxyethylrutoside, a hydroxyethylquercetin-7-O-glucuronide, a compound of any of Structural Formulas I-IV), or a pharmaceutically acceptable salt thereof, can also be administered in combination with one or more other therapies or treatments, e.g., additional therapeutic agents. With respect to the administration of a compound in combination with one or more other therapies or treatments (adjuvant, targeted, and the like), the agent is typically administered as a single dose (by, e.g., injection, infusion, orally), followed by repeated doses at particular intervals (e.g., one or more hours) if desired or indicated.

When administered in a combination therapy, the compound, or a pharmaceutically acceptable salt thereof, can be administered before, after or concurrently with the other therapy (e.g., an additional agent(s)). When co-administered simultaneously (e.g., concurrently), the compound, or a pharmaceutically acceptable salt thereof, and other therapy can be in separate formulations or the same formulation. Alternatively, the compound, or a pharmaceutically acceptable salt thereof, and other therapy can be administered sequentially, as separate compositions, within an appropriate time frame as determined by a skilled clinician (e.g., a time sufficient to allow an overlap of the pharmaceutical effects of the therapies).

The actual dose of a therapeutic agent and treatment regimen can be determined by the physician or clinician, taking into account the nature of the disease, other therapies being given, and subject characteristics.

EXEMPLIFICATION

Example 1

This non-limiting prophetic example describes embodiments of compositions of the invention.

A flavone glucuronide pharmaceutical composition comprises:

| | |
|---|---|
| Flavone glucuronide | 450 mg |
| Gelatin | 31 mg |
| Magnesium Stearate | 4 mg |
| Microcrystalline cellulose | 62 mg |
| Sodium starch glycollate | 27 mg |
| Talc | 6 mg |

Optionally, the composition may comprise other flavonoids, such as hesperidin at 50 mg.

Likewise, a flavone glucuronate salt pharmaceutical composition comprises:

| | |
|---|---|
| Flavone glucuronate salt (as glucuronide) | 450 mg |
| Gelatin | 31 mg |
| Magnesium Stearate | 4 mg |
| Microcrystalline cellulose | 62 mg |
| Sodium starch glycollate | 27 mg |
| Talc | 6 mg |

Optionally, the composition may comprise other flavonoids, such as hesperidin at 50 mg.

Likewise, a hydroxyethylquercetin-7-O-glucuronide pharmaceutical composition comprises:

| | |
|---|---:|
| Hydroxyethylquercetin-7-O-glucuronide | 450 mg |
| Gelatin | 31 mg |
| Magnesium Stearate | 4 mg |
| Microcrystalline cellulose | 62 mg |
| Sodium starch glycollate | 27 mg |
| Talc | 6 mg |

Optionally, the composition may comprise other flavonoids, such as hesperidin at 50 mg.

The relevant teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A pharmaceutical composition comprising from about 5% to about 95% weight/weight of a hydroxyethylquercetin-O-glucuronide, or a pharmaceutically acceptable salt thereof, and a pharmaceutically acceptable carrier or diluent.

2. The pharmaceutical composition of claim 1, wherein the composition is formulated for oral administration.

3. The pharmaceutical composition of claim 1, further comprising a second acid.

4. The pharmaceutical composition of claim 3, wherein the second acid is citric acid or hydrochloric acid or a combination thereof.

5. The pharmaceutical composition of claim 1, wherein the hydroxyethylquercetin-O-glucuronide is a hydroxyethylquercetin-3-O-glucuronide.

6. A pharmaceutical composition comprising from about 5% to about 95% weight/weight of a hydroxyethylquercetin-5-O-glucuronide, or a pharmaceutically acceptable salt thereof, and a pharmaceutically acceptable carrier or diluent.

7. A pharmaceutical composition comprising from about 5% to about 95% weight/weight of a hydroxyethylquercetin-3'-O-glucuronide, or a pharmaceutically acceptable salt thereof, and a pharmaceutically acceptable carrier or diluent.

8. A pharmaceutical composition comprising from about 5% to about 95% weight/weight of a hydroxyethylquercetin-4'-O-glucuronide, or a pharmaceutically acceptable salt thereof, and a pharmaceutically acceptable carrier or diluent.

9. A pharmaceutical composition comprising from about 5% to about 95% weight/weight of a monohydroxyethylquercetin-O-glucuronide, or a pharmaceutically acceptable salt thereof, and a pharmaceutically acceptable carrier or diluent.

10. The pharmaceutical composition of claim 9, wherein the monohydroxyethylquercetin-O-glucuronide is a mono-3'-O-hydroxyethyl quercetin-O-glucuronide.

11. A pharmaceutical composition comprising a mono-4'-O-hydroxyethylquercetin-O-glucuronide, or a pharmaceutically acceptable salt thereof, and a pharmaceutically acceptable carrier or diluent.

12. A method of inhibiting norepinephrine metabolism in a subject in need thereof, comprising:
    administering to the subject an effective amount of the pharmaceutical composition of claim 1.

13. The method of claim 12, wherein the administering is orally administering.

14. The method of claim 12, further comprising administering an acidifier.

15. The method of claim 14, wherein the acidifier is betaine, or a pharmaceutically acceptable salt thereof.

16. The method of claim 14, wherein the acidifier is acidic liquid media.

17. The method of claim 16, wherein the acidic liquid media has a pH of less than about 3.

18. The method of claim 17, wherein the acidic liquid media comprises citric acid, acetic acid, or hydrochloric acid, or a combination of any of the foregoing.

19. The method of claim 16, wherein the acidic liquid media comprises vinegar or a citrus juice, or a combination of the foregoing.

* * * * *

UNITED STATES PATENT AND TRADEMARK OFFICE
CERTIFICATE OF CORRECTION

PATENT NO. : 11,304,968 B2
APPLICATION NO. : 16/563620
DATED : April 19, 2022
INVENTOR(S) : Thomas M. DiMauro It is certified that error appears in the above-identified patent and that said Letters Patent is hereby corrected as shown below:

In the Claims

In Claim 11, Column 22, Line 15, delete "A pharmaceutical composition comprising" and insert --The pharmaceutical composition of claim 9, wherein the monohydroxyethylquercetin-O-glucuronide is--

In Claim 11, Column 22, Lines 16-18, delete ", or a pharmaceutically acceptable salt thereof, and a pharmaceutically acceptable carrier or diluent"

Signed and Sealed this
Ninth Day of August, 2022

*Katherine Kelly Vidal*

Katherine Kelly Vidal
*Director of the United States Patent and Trademark Office*